(12) United States Patent
Kan et al.

(10) Patent No.: US 9,517,027 B2
(45) Date of Patent: Dec. 13, 2016

(54) ADVANCEMENT MECHANISM FOR CARTRIDGE-BASED DEVICES

(75) Inventors: Gil Kan, Atlanta, GA (US); Brian M. Collins, Denver, CO (US); Gregory Lamps, Smyrna, GA (US)

(73) Assignee: FACET TECHONOLOGIES, LLC, Atlanta, GA (US)

( * ) Notice: Subject to any disclaimer, the term of this patent is extended or adjusted under 35 U.S.C. 154(b) by 1305 days.

(21) Appl. No.: 12/892,324

(22) Filed: Sep. 28, 2010

(65) Prior Publication Data

US 2011/0130782 A1  Jun. 2, 2011

Related U.S. Application Data

(63) Continuation-in-part of application No. 12/522,764, filed on Jul. 10, 2009, now abandoned, which is a
(Continued)

(51) Int. Cl.
*A61B 5/00* (2006.01)
*A61B 5/151* (2006.01)
*A61B 5/15* (2006.01)

(52) U.S. Cl.
CPC ......... *A61B 5/15182* (2013.01); *A61B 5/1411* (2013.01); *A61B 5/1513* (2013.01);
(Continued)

(58) Field of Classification Search
CPC ............... A61B 5/15113; A61B 5/1513; A61B 5/15132; A61B 5/15146; A61B 5/15161; A61B 5/15182; A61B 5/15126; A61B 5/15148; A61B 5/15151
(Continued)

(56) References Cited

U.S. PATENT DOCUMENTS 3,760,809 A  9/1973  Campbell, Jr.
4,643,189 A  2/1987  Mintz
(Continued)

FOREIGN PATENT DOCUMENTS

CA  2700330 A1  3/2009
DE  10057832 C1  2/2002
(Continued)

OTHER PUBLICATIONS

International Search Report and Written Opinion for PCT/US05/23155; Feb. 15, 2008; 8 pgs.
(Continued)

*Primary Examiner* — Devin Henson
(74) *Attorney, Agent, or Firm* — Gardner Groff Greenwald & Villanueva, PC

(57) ABSTRACT

An advancement mechanism of a lancing device operates to sequentially advance lancets in a cartridge. The advancement mechanism includes a rotary drive gear assembly with a first gear and a second gear that co-rotate in a first angular direction by operation of an inter-gear unidirectional drive mechanism such as a ratcheting mechanism. A second-gear unidirectional lock mechanism, such as a ratcheting mechanism, locks the second drive gear from co-rotating with the first drive gear in a second opposite angular direction without impeding rotation in the first direction. The second gear directly or indirectly rotationally drives a pinion gear, which rotationally drives a cartridge gear to advance the lancets in indexed increments for use. The first drive gear is rotated in the first and second directions by a rack gear of a translating operating handle. In addition, a rotary-gear cap-displacement mechanism and a rotary-gear charging/actuation mechanism are provided in other embodiments.

18 Claims, 18 Drawing Sheets

Related U.S. Application Data continuation-in-part of application No. 12/522,765, filed on Jul. 10, 2009, now Pat. No. 8,221,332.

(60) Provisional application No. 61/246,223, filed on Sep. 28, 2009.

(52) U.S. Cl.
CPC .... *A61B 5/150022* (2013.01); *A61B 5/15113* (2013.01); *A61B 5/15117* (2013.01); *A61B 5/15132* (2013.01); *A61B 5/15146* (2013.01); *A61B 5/15151* (2013.01); *A61B 5/15161* (2013.01); *A61B 5/150175* (2013.01); *A61B 5/150259* (2013.01); *A61B 5/150412* (2013.01); *A61B 5/150702* (2013.01); *A61B 50/3001* (2016.02); *A61B 5/15126* (2013.01); *A61B 5/15148* (2013.01)

(58) Field of Classification Search
USPC .......................................... 600/583; 606/181
See application file for complete search history.

(56) References Cited

U.S. PATENT DOCUMENTS

| | | | |
|---|---|---|---|
| 4,787,398 A | 11/1988 | Garcia et al. | |
| 4,794,926 A | 1/1989 | Munsch et al. | |
| 4,823,806 A | 4/1989 | Bajada | |
| 5,035,704 A | 7/1991 | Lambert et al. | |
| 5,196,025 A | 3/1993 | Ranalletta et al. | |
| 5,279,294 A | 1/1994 | Anderson et al. | |
| 5,297,922 A | 3/1994 | Sieg | |
| 5,318,583 A | 6/1994 | Rabenau et al. | |
| 5,514,152 A | 5/1996 | Smith | |
| 5,527,333 A | 6/1996 | Nikkels et al. | |
| 5,545,174 A | 8/1996 | Schenk et al. | |
| 5,628,764 A | 5/1997 | Schraga | |
| 5,628,765 A | 5/1997 | Morita | |
| 5,645,555 A | 7/1997 | Davis et al. | |
| 5,738,244 A | 4/1998 | Charlton et al. | |
| RE35,803 E | 5/1998 | Lange et al. | |
| 5,776,157 A | 7/1998 | Thorne et al. | |
| 5,871,494 A | 2/1999 | Simons et al. | |
| 5,951,492 A | 9/1999 | Douglas et al. | |
| 5,971,941 A | 10/1999 | Simons et al. | |
| 6,036,924 A | 3/2000 | Simons et al. | |
| 6,156,050 A | 12/2000 | Davis et al. | |
| 6,228,100 B1 | 5/2001 | Schraga | |
| D447,566 S | 9/2001 | LeVaughn et al. | |
| 6,306,152 B1 | 10/2001 | Verdonk et al. | |
| D458,127 S | 6/2002 | de Groote | |
| 6,472,220 B1 | 10/2002 | Simons et al. | |
| 6,530,892 B1 | 3/2003 | Kelly | |
| 6,540,675 B2 | 4/2003 | Aceti et al. | |
| 6,616,616 B2 | 9/2003 | Fritz et al. | |
| 6,783,537 B1 | 8/2004 | Kuhr et al. | |
| 6,929,649 B2 | 8/2005 | Pugh | |
| 7,001,344 B2 | 2/2006 | Freeman et al. | |
| 7,025,774 B2 | 4/2006 | Freeman et al. | |
| 7,141,058 B2 | 11/2006 | Briggs et al. | |
| 7,144,404 B2 | 12/2006 | Whitson et al. | |
| 7,150,755 B2 | 12/2006 | LeVaughn et al. | |
| 7,175,642 B2 | 2/2007 | Briggs et al. | |
| 7,198,606 B2 | 4/2007 | Boecker et al. | |
| 7,226,461 B2 | 6/2007 | Boecker et al. | |
| 7,229,458 B2 | 6/2007 | Boecker et al. | |
| 7,232,451 B2 | 6/2007 | Boecker et al. | |
| 7,244,265 B2 | 7/2007 | Freeman et al. | |
| 7,291,117 B2 | 11/2007 | Boecker et al. | |
| 7,297,122 B2 | 11/2007 | Boecker et al. | |
| 7,297,151 B2 | 11/2007 | Boecker et al. | |
| 7,331,931 B2 | 2/2008 | Freeman et al. | |
| 7,343,188 B2 | 3/2008 | Sohrab | |
| 7,344,507 B2 | 3/2008 | Briggs et al. | |
| 7,377,904 B2 | 5/2008 | Conway et al. | |
| 7,470,400 B2 | 12/2008 | Uchigaki et al. | |
| 7,582,063 B2 | 9/2009 | Wurster et al. | |
| 7,666,149 B2 | 2/2010 | Simons et al. | |
| 7,837,633 B2 | 11/2010 | Conway et al. | |
| 7,883,473 B2 | 2/2011 | LeVaughn et al. | |
| 7,909,791 B2 | 3/2011 | Liniger et al. | |
| 2002/0052618 A1 | 5/2002 | Haar et al. | |
| 2004/0230216 A1* | 11/2004 | Levaughn et al. | 606/181 |
| 2005/0154410 A1 | 7/2005 | Conway et al. | |
| 2006/0157362 A1 | 7/2006 | Schraga | |
| 2006/0161078 A1 | 7/2006 | Schraga | |
| 2006/0241666 A1 | 10/2006 | Briggs et al. | |
| 2006/0241667 A1 | 10/2006 | Freeman | |
| 2010/0057119 A1 | 3/2010 | Robbins et al. | |
| 2010/0094326 A1 | 4/2010 | Robbins | |
| 2010/0106174 A1 | 4/2010 | Conway et al. | |
| 2010/0174211 A1 | 7/2010 | Frey et al. | |
| 2010/0286563 A1* | 11/2010 | Bryer et al. | 600/583 |

FOREIGN PATENT DOCUMENTS

| | | |
|---|---|---|
| DE | 20213607 U1 | 8/2002 |
| DE | 10208575 C1 | 8/2003 |
| DE | 10245721 A1 | 12/2003 |
| EP | 0811843 A2 | 12/1997 |
| WO | 03070099 A1 | 8/2003 |
| WO | 03071940 A1 | 9/2003 |
| WO | 2005018425 A2 | 3/2005 |
| WO | 2005018430 A2 | 3/2005 |
| WO | 2005018709 A2 | 3/2005 |
| WO | 2005018710 A2 | 3/2005 |
| WO | 2005018711 A2 | 3/2005 |
| WO | 2006004859 A2 | 1/2006 |
| WO | 2008028571 A1 | 3/2008 |
| WO | 2008138443 A1 | 11/2008 |
| WO | 2009037341 A1 | 3/2009 |
| WO | 2011038386 A2 | 3/2011 |

OTHER PUBLICATIONS

International Preliminary Report on Patentability for PCT/US05/23155; Mar. 17, 2009; 6 pgs.
International Search Report and Written Opinion for PCT/US08/50858; Nov. 21, 2008; 8 pgs.
International Preliminary Report on Patentability for PCT/US08/50858; Jul. 23, 2009; 7 pgs.
International Search Report of PCT/US08/68708; Sep. 15, 2008; 2 pgs.
International Preliminary Report on Patentability of PCT/US08/68708; Jan. 5, 2010; 5 pgs.
ISR and Written Opinion of PCT/US2010/050513; Jun. 29, 2011; 14 pgs.
Japanese Office Action for App. No. 2012-531111; Jul. 1, 2014; 6 pgs.

* cited by examiner

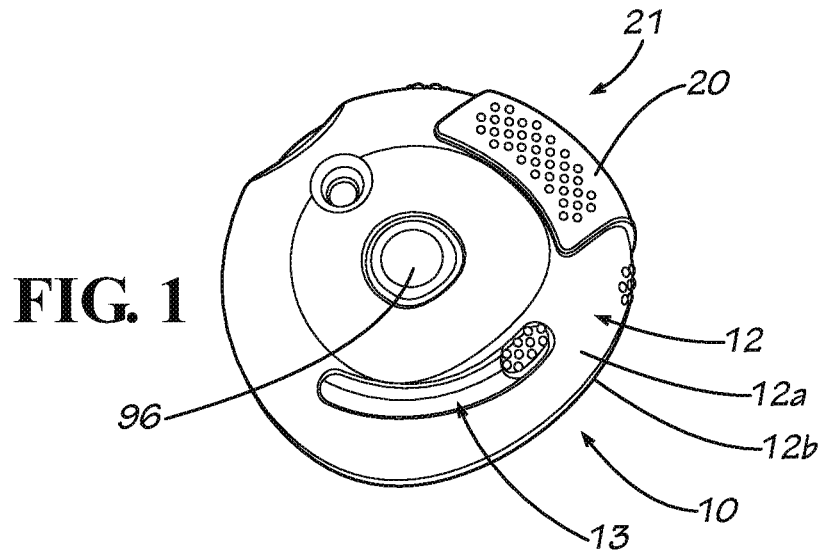
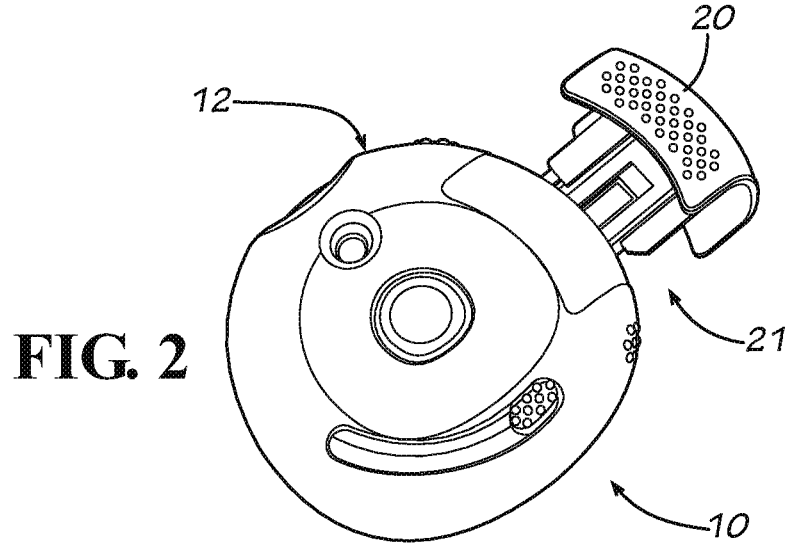
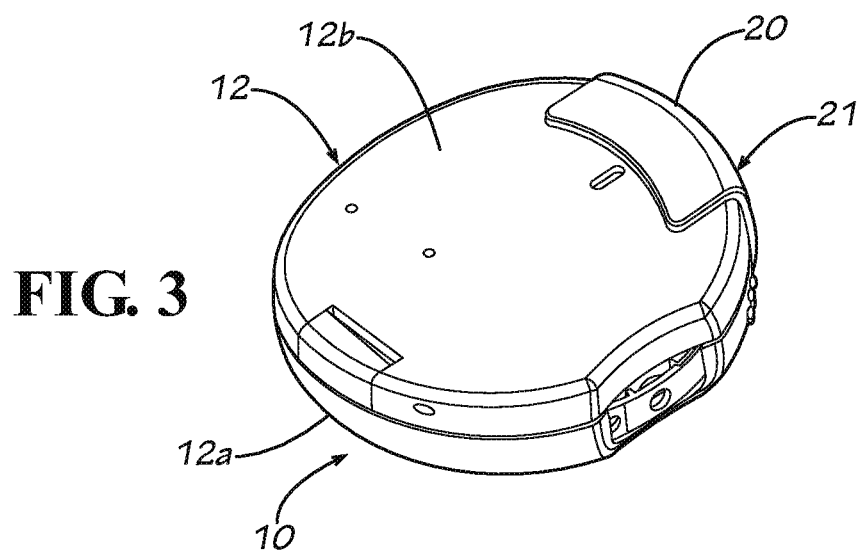

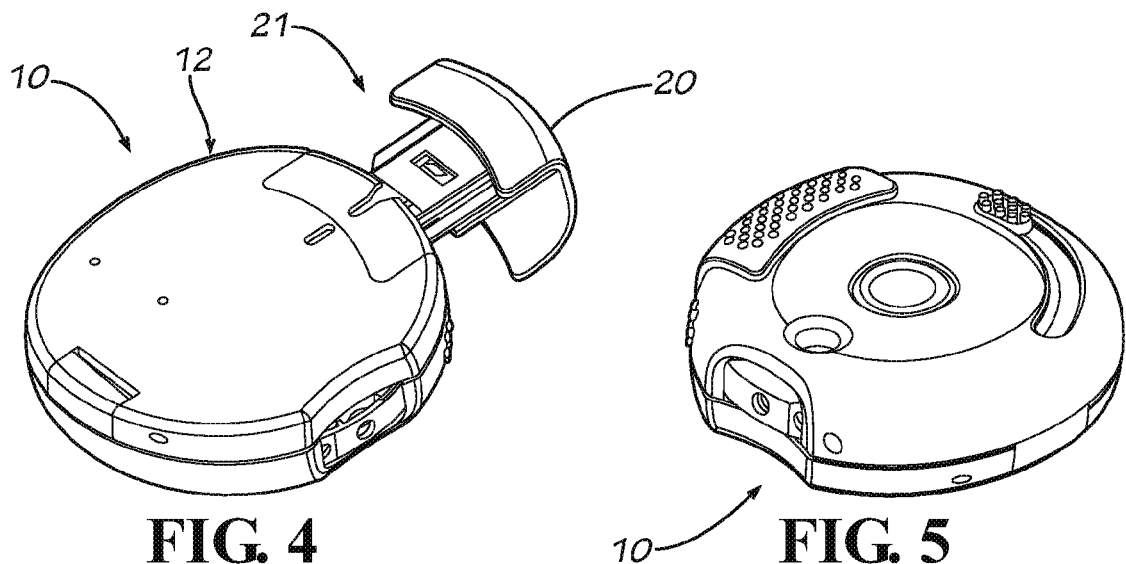
FIG. 4  FIG. 5
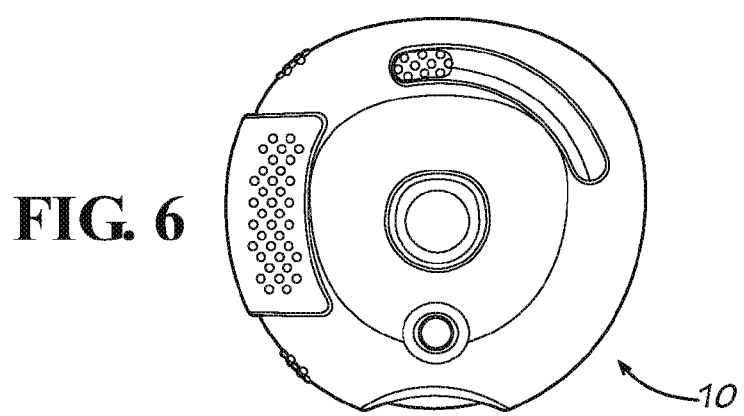
FIG. 6
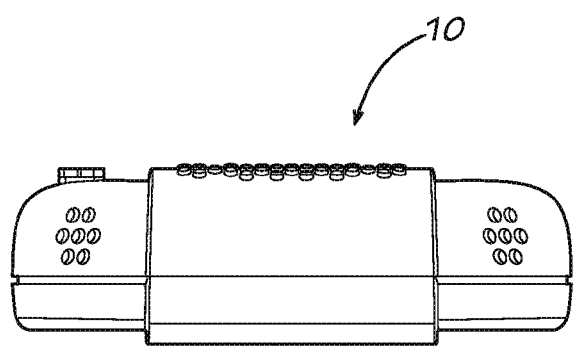
FIG. 7

ADVANCEMENT MECHANISM FOR CARTRIDGE-BASED DEVICES

CROSS-REFERENCE TO RELATED APPLICATIONS

This application claims the priority benefit of U.S. Provisional Patent Application Serial No. 61/246,223, filed Sep. 28, 2009, and is a continuation-in-part of U.S. Patent Applications Ser. Nos. 12/522,764 and 12/522,765, both filed Jul. 10, 2009, the entireties of which are hereby incorporated herein by reference for all purposes.

TECHNICAL FIELD

The present invention relates generally to cartridge-based devices and, more particularly, to advancement mechanisms for medical or other devices using cartridges holding one or more lancets or other items for use or dispensing.

BACKGROUND

Cartridge-based devices can be utilized to dispense or apply certain medical items, such as medicine, lancets, sutures, needles, surgical staples, etc., or other medical or other items. For example, a replaceable cartridge containing a plurality of items for sequential use may be loaded into a tool or other device. Such devices can be manufactured to interface with humans directly or machines utilizing the items therein. For example, many medical procedures require puncturing of the skin, and sometimes underlying tissues, of an animal or human subject. A sharp lancet tip is commonly used to puncture the subject's skin at a lancing site to obtain a sample of blood, interstitial fluid, or other body fluid, as for example in blood-glucose monitoring by diabetics and in blood-typing and blood-screening applications.

In some situations, a person must periodically sample their blood for multiple testing throughout the day or week. This is typically done using a lancing device of some sort. Because re-use of a lancet can result in infection or spread of blood-borne contaminants, persons requiring repeated testing often must carry multiple lancets with them, with each lancet separately loaded into the lancing device for each sampling. This can be inconvenient and may lead to reduced compliance with a prescribed test regimen.

Cartridge-type lancing devices have been developed to allow the user to load cartridges into the lancing device, each cartridge holding multiple lancets for sequential use. These cartridge-type lancing devices typical operate by advancing each of the lancets in the cartridge for use, charging a drive spring, and, upon actuation of an actuator, releasing the lancet to be propelled by the discharging drive spring through a lancing stroke. In addition, for cartridges holding lancets with sterility caps on their puncturing tips, typical lancing devices also operate to remove the sterility caps from the lancet puncturing tips before the lancing stroke. Furthermore, some lancing devices are also operable to provide adjustment for different puncturing depths of the lancet tip. However, existing cartridge-type lancing devices have not proven entirely satisfactory in their convenience, ease-of-use, cost, reliability, and/or effectiveness.

Accordingly, it can be seen that needs exist for improvements in advancement, de-capping, depth-adjustment, and charging mechanisms for cartridge-based devices. It is to the provision of an improved cartridge-based device and cartridge meeting these and other needs that the present invention is primarily directed.

SUMMARY

The present invention relates to cartridge-based devices including an innovative advancement mechanism, charging/actuation mechanism, and/or displacement mechanism. In the depicted embodiments, the device is adapted for use with a cartridge holding an array of lancets. In alternative embodiments, the device is adapted for use with a cartridge holding other items for sequential use and/or dispensing.

The lancing devices of the depicted embodiments include a housing and an operating handle that translates between a retracted position (against the housing) and an extended position (slid away from the housing). The operating handle includes a grip and at least one rack gear. The grip can be grasped by a user to pull and push the operating handle through one pull/push operating cycle. And the rack gear(s) translate within the housing to operate one or more of the operational assemblies of the lancing device.

In a first example embodiment, an advancement mechanism is operable to sequentially advance the lancets in the cartridge for use. The advancement mechanism includes a rotary drive gear assembly with a first drive gear and a second drive gear that co-rotate in a first angular direction by operation of an inter-gear unidirectional drive mechanism. The advancement mechanism can also include a second-gear unidirectional lock mechanism that locks the second drive gear from co-rotation with the first drive gear in a second opposite angular direction without impeding rotation in the first direction. The first gear is rotationally driven in the first and second angular directions by the rack gear of the operating handle, for example, when the handle is pulled out and pushed in, respectively.

The inter-gear unidirectional drive mechanism can be provided by a ratcheting drive mechanism. In the depicted embodiment, the ratcheting drive mechanism includes at least one pawl defining a catch surface, at least one ratchet tooth defining a catch surface, and a ramped disengagement surface defined for example by the at least one ratchet tooth. The catch surfaces oppose each other so that when the first drive gear is rotationally driven in the first direction by the rack gear of the operating handle (e.g., when the handle is pulled out), the second drive gear is co-rotated with it. But when the first drive gear is rotationally driven in the second opposite direction by the rack gear (e.g., when the handle is pushed in), the catch surfaces do not oppose each other so the second drive gear is not co-rotated with the first drive gear. And the ramped disengagement surface displaces the pawl catch surface temporarily so that that the pawl can clear the tooth and then reset for future opposing engagement by the catch surfaces.

The second-gear unidirectional lock mechanism can be provided by a ratcheting lock mechanism. In the depicted embodiment, the ratcheting lock mechanism includes at least one pawl defining a lock surface, at least one ratchet tooth defining a lock surface, and a ramped disengagement surface defined for example by the at least one pawl. The lock surfaces oppose each other so that when the first drive gear is rotationally driven in the second opposite direction by the rack gear, the second drive gear is locked from co-rotating with it. But when the first drive gear is rotationally driven in the first direction by the rack gear, the lock surfaces do not oppose each other so the second drive gear is free to co-rotate with the first drive gear. And the ramped disengagement surface displaces the pawl lock surface temporarily so that that the pawl can clear the tooth and then reset for future opposing engagement by the lock surfaces.

The second gear directly or indirectly rotationally drives a pinion gear, which rotationally drives a cartridge gear to advance the lancets in indexed increments for use. The second drive gear can function as the pinion gear, a multi-gear pinion gear assembly can be provided for gear-reduction purposes, and/or an intermediate idler gear assembly can be provided for gear-reduction purposes.

In addition, a rotary-gear cap-displacement mechanism is provided for displacing the sterility cap of the active-positioned lancet. The cap-displacement mechanism includes a rotary lifter gear, a semi-circular lifting ramp formed on the lifter gear, and a lifter structure. When the lifter gear is rotated, the lifting ramp is rotated into engagement with the lifter. As the lifting ramp is rotated across the lifter, it pushes the lifter into engagement with the removed lancet cap to push it out of the lancing stroke path. The lifter gear can be driven by the same or a different rack gear as that used to operate the advancement mechanism.

Furthermore, a rotary-gear charging mechanism is provided for retracting an active-positioned lancet, charging a drive spring and, upon actuation of the actuation mechanism, releasing the lancet to be propelled by the discharging drive spring through a lancing stroke. The charging mechanism can include a guide element, a piston, a drive spring, and a return spring. The piston engages the active lancet and drives it through its lancing stroke. The drive spring propels the piston (and thus the active lancet) forward in its lancing stroke and the return spring biases it backward fully into the housing. The guide is positioned on the cap-displacement rotary gear or on a separate rotary gear. The guide includes an eccentrically curved cam surface that travels across a follower surface of the piston when the rotary gear is rotated. The cam surface thereby guides the piston backward to retract the lancet to the retracted/charged position. The rotary gear can be driven by the same or a different rack gear as that used to operate the advancement and/or cap-displacement mechanisms.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of example embodiments of the invention, and are not restrictive of the invention, as claimed.

BRIEF DESCRIPTION OF THE DRAWINGS

FIG. 1 is a top perspective view of a cartridge-based lancing device according to a first example embodiment of the present invention, showing an operating handle in a retracted position.

FIG. 2 shows the lancing device of FIG. 1 with the operating handle in an extended position.

FIG. 3 is a bottom perspective view of the lancing device of FIG. 1.

FIG. 4 is a bottom perspective view of the lancing device of FIG. 2.

FIG. 5 is another top perspective view of the lancing device of FIG. 1.

FIG. 6 is a plan view of the lancing device of FIG. 1.

FIG. 7 is a left side view of the lancing device of FIG. 6.

DETAILED DESCRIPTION OF EXAMPLE EMBODIMENTS

Figure 8:
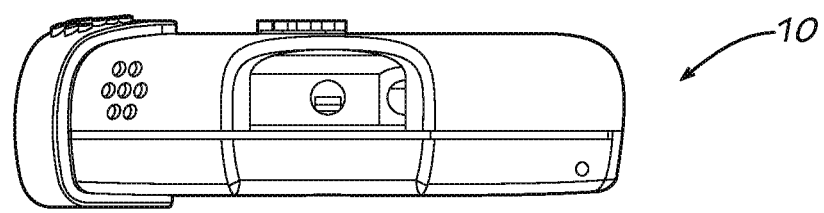
FIG. 8 is a front side view of the lancing device of FIG. 6.
Figure 9:
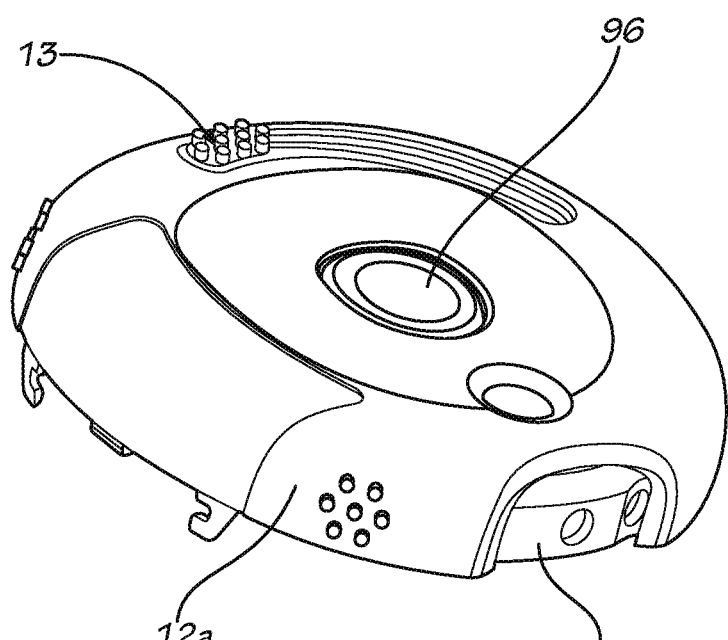
FIG. 9 is a top perspective view of a housing top of the lancing device of FIG. 1.
Figure 10:
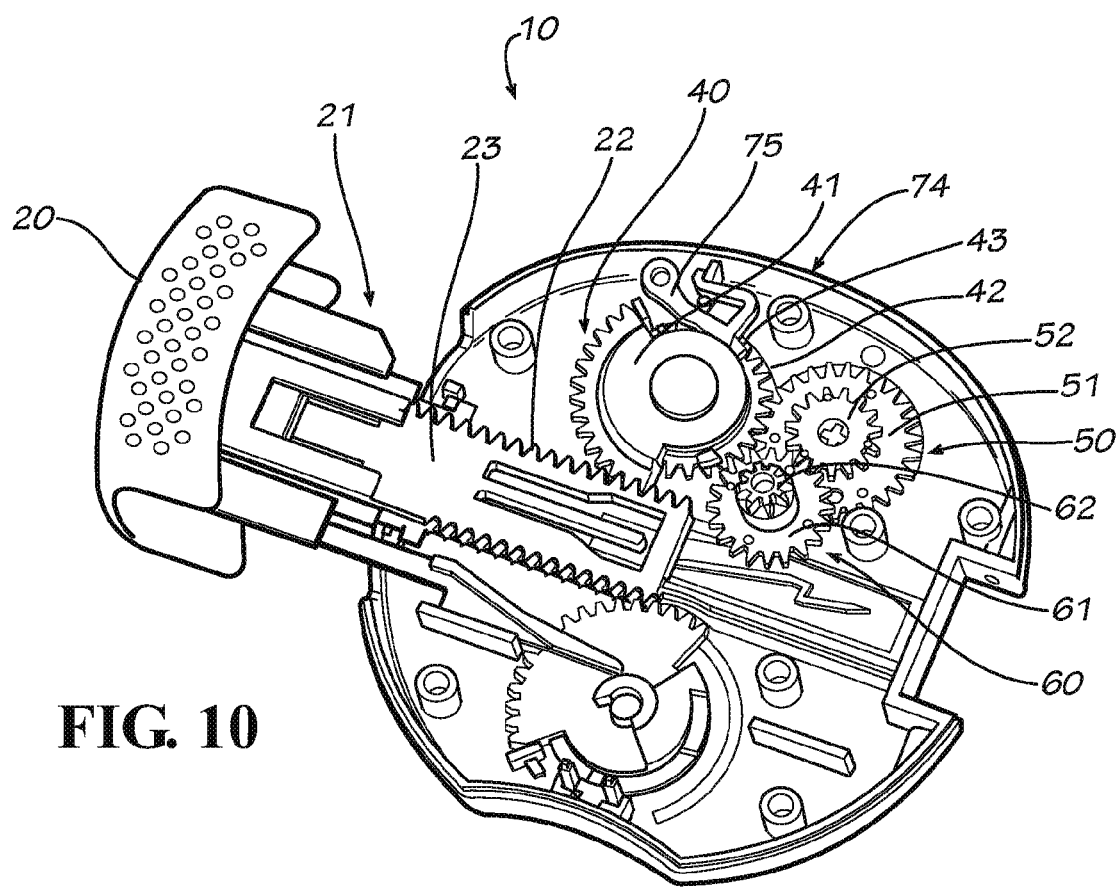
FIG. 10 is a top perspective view of the lancing device of FIG. 1, with the housing top and a housing bottom internal cover removed to reveal the internal advancement mechanism.
Figure 11:
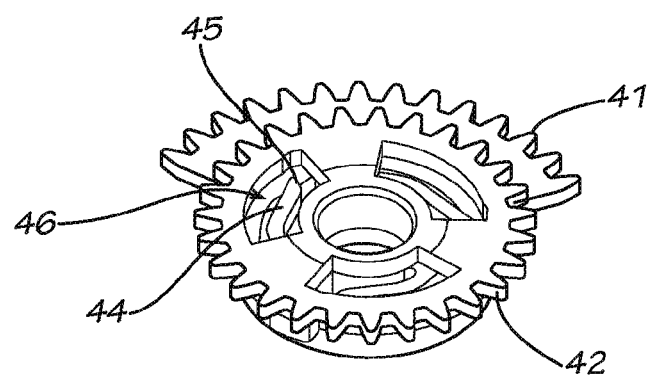
FIG. 11 is a bottom perspective view of a ratchet gear assembly of the advancement mechanism of FIG. 10.
Figure 12:
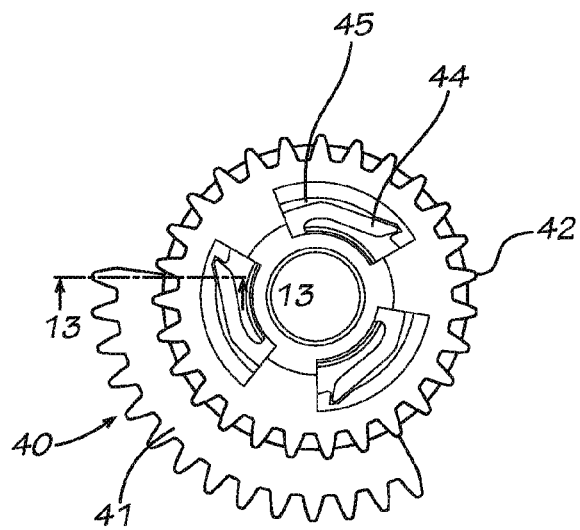
FIG. 12 is a bottom view of the ratchet gear assembly of FIG. 11.
Figure 13:
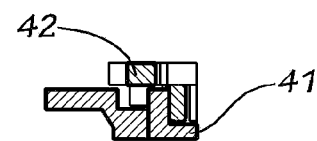
FIG. 13 is a cross-sectional view of the ratchet gear assembly taken at line 13-13 of FIG. 12.
Figure 14:
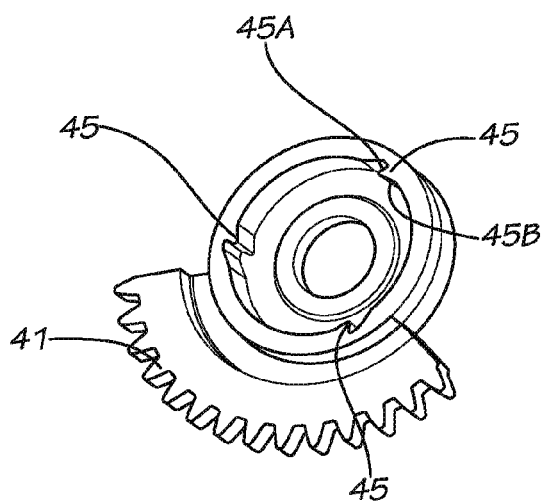
FIG. 14 is a bottom perspective view of a first gear of the ratchet gear assembly taken of FIG. 11.
Figure 15:
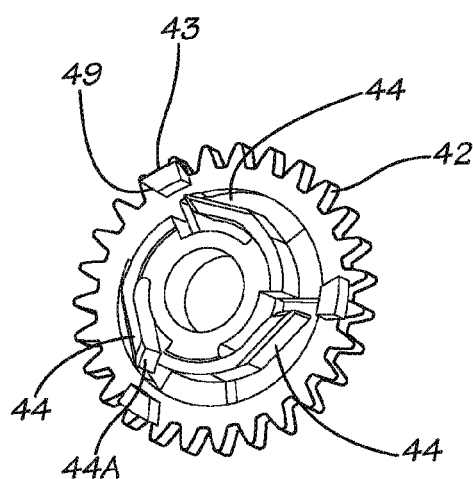
FIG. 15 is a top perspective view of a second gear of the ratchet gear assembly taken of FIG. 11.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, wherein like reference numbers represent corresponding parts throughout the several views, FIGS. 1-46 show a lancing device 10 according to a first embodiment of the present invention. The lancing device 10 is used with a cartridge 80 holding a plurality of lancets 82 (see FIGS. 27-32). It will be understood that the term "cartridge" as used herein includes carrousels, carriers, and other types of dispensers, whether they are replaceable cartridges used with re-useable lancing devices or whether they are integral to and disposable with the lancing devices after all the lancets have been used once. In addition, it will be understood that instead of a lancing device used with a cartridge of lancets, the herein described assemblies and aspects of the invention can be embodied in other medical devices, construction tools, or other devices using cartridges holding other items that are advanced for use or dispensing. For example, the advancement mechanism described herein can be adapted for use in devices that dispense sutures, needles, medicines, or surgical staples.

The housings, gears, actuators, and/or other components of the lancing device 10 and cartridge 80 can be fabricated from conventional materials using conventional fabrication techniques. Thus, these components can be made of plastics, metals, or other suitable materials known in the art, by molding, machining, stamping or other suitable processes known in the art.

The lancing device 10 of the depicted embodiment includes a depth-adjustment mechanism 13, an advancement mechanism 30, a lancet cap-displacement mechanism mechanism 100, a charging mechanism 90, and an actuation mechanism 16. The depth-adjustment mechanism 13 (see FIGS. 1-9) operates to provide adjustment for different puncturing depths of the lancet tip into the user's skin. The advancement mechanism 30 (see FIGS. 10-26) operates to sequentially advance the lancets for use. The cap-displacement mechanism 100 (see FIGS. 10 and 44-46) operates to remove the sterility caps from the lancet puncturing tips before the lancing stroke. The charging mechanism 90 (see FIGS. 10 and 33-43) operates to retract an active-positioned lancet, charge a drive spring and, upon actuation of the actuation button, release the lancet to be propelled by the discharging drive spring through a lancing stroke. And the actuation mechanism 16 (see FIG. 33) operates to release the lancet from the charged position so that it can be propelled by the discharging drive spring through its lancing stroke.

FIGS. 1-9 show a housing 12 and an operating handle 21 of the lancing device 10. The housing 12 can include a top portion 12a and a bottom portion 12b that can be at least partially separable (e.g., pivotally in a clamshell arrangement) to an open position for replacing the lancet cartridges. The operating handle 21 is translationally mounted to the housing 12 so that it slides between a retracted position (see FIG. 1) and an extended position (see FIG. 2). The operating handle 21 includes a grip portion 20 for a user to grasp to push and pull the handle between the retracted and extended positions. The grip 20 can have a C-shaped side profile so that it overlaps with the top and bottom sides of the housing 12 to retain the top and bottom housing portions 12a and 12b in a closed position when the operating handle 21 is in the retracted position, as depicted. And the operating handle 21 and the housing 12 have cooperating stop surfaces that abut each other to limit the translating travel of the operating handle 21 between the retracted and extended positions.

FIGS. 10-20 show structural details of the advancement mechanism 30, which is housed within the housing 12. The depicted advancement mechanism 30 includes an advancement handle gear 22, a drive gear assembly 40, a unidirectional inter-gear co-rotation drive assembly such as a ratcheting drive assembly 46, a unidirectional second-gear rotation lock assembly such as a ratcheting lock assembly 70, an intermediate idler gear assembly 50, and a pinion gear assembly 60.

The advancement handle gear 22 is defined by or mounted to the operating handle 21. In the depicted embodiment, the handle gear is provided by a rack gear 22. For example, the rack gear 22 can be formed along a side of an elongate member 23, such as the depicted thin rectangular structure, that extends from the grip 20 and into the housing 12. Thus, as the grip 20 is manipulated to slide the handle 21 between the retracted and extended positions, the rack gear 22 translates within the housing 12. In alternative embodiments, the operating handle is rotary, translating, or both, and/or includes one or more rotary gears (instead of rack gears) that drive the operational assemblies of the lancing device.

The drive gear assembly 40 includes a first rotary drive gear 41 and a second rotary drive gear 42 that are mounted on the same rotational axis. The first gear 41 is engaged and rotationally driven by the rack gear 22 in a first angular direction and an opposite second angular direction as the rack gear translates within the housing 12 when the operating handle 21 is slid between the retracted and extended positions. The first gear 41 can include teeth along its entire circumference or, as depicted, only along a portion thereof.

The inter-gear unidirectional drive assembly operably interconnects the first and second drive gears 41 and 42 so that the second gear is driven by and rotates with the first gear in the first direction but is not driven in co-rotation by the first gear in the opposite second direction. In particular, the inter-gear unidirectional drive assembly includes at least one catch surface defined by or extending from an element of each of the first and second drive gears 41 and 42. The catch surfaces are each engaged to maintain the two gears in co-rotation in the first direction, with at least one of the catch surfaces not engaged when the first gear rotates in the opposite second direction. Such disengagement can be caused by at least one disengagement surface that moves a movable one of the elements defining at least one of the catch surfaces.

For example, the inter-gear unidirectional drive assembly can be provided by an inter-gear ratcheting drive assembly including at least one pawl element and at least one tooth element that is operably engaged by the pawl. The pawl can extend from one of the first and second drive gears, and the tooth can extend from the other one of the first and second drive gears. The pawl defines one of the catch surfaces and the tooth defines the other one of the catch surfaces. One or more ramped disengagement surfaces are defined by the pawl and/or the tooth and are positioned adjacent that catch surface. The ramped disengagement surface(s) can be linear, curved, or a combination thereof.

In operation, the catch surfaces oppose each other so that, when the first drive gear is rotated in the first direction, the first gear catch surface contacts the second gear catch surface to rotationally drive the second drive gear along with the first drive gear. But when the first gear is rotated in the second opposite direction, the first gear catch surface is rotated away from the second gear catch surface, so the second gear is not rotationally driven by the first gear. And when the first gear is rotated further in the second angular direction, the ramped surface is engaged by the pawl or the tooth to temporarily displace (from the engaged to the disengaged position) at least one of the catch surfaces so that the first gear catch surface rotates past the second gear catch surface. Once the ramped surface has been cleared, the pawl or the tooth returns to the engaged position so that the catch surfaces are again in an opposing relationship with each other so that rotating the first gear again causes the second gear to rotate with it.

In the ratcheting drive assembly 46 of the depicted embodiment (see FIGS. 10-17), the at least one pawl is provided by three cantilevered resilient pawl arms 44 each extending from the second drive gear 42 in a generally spiral arrangement. And the at least one tooth is provided by three ratchet drive teeth 45 (e.g., formed in part by three notches) in an inner circular surface of the first drive gear 41. The resilient arms 44 include catch surfaces 44a, and the teeth 45 include catch surfaces 45a and ramped surfaces 45b. The resilient arms 44 are made of a resilient, flexible material selected so that they resiliently deflect from engaged positions engaging the ratcheting drive teeth 45, to disengaged positions deflected from engagement with the ratchet drive teeth, and resiliently back to the engaged positions. The resilient arms 44 and the ratchet drive teeth 45 can be made as integral features of, or separate structures coupled to, the second gear 42 and the first gear 41, respectively. The ratchet drive teeth 45 are preferably separate structures from the gear teeth of the first gear 41 (in the depicted embodiment, the ratchet teeth and the gear teeth are positioned along coaxial circles with different radii and in different rotational planes, with the ratchet teeth not designed for gear-meshing in a gear train).

Figure 16:
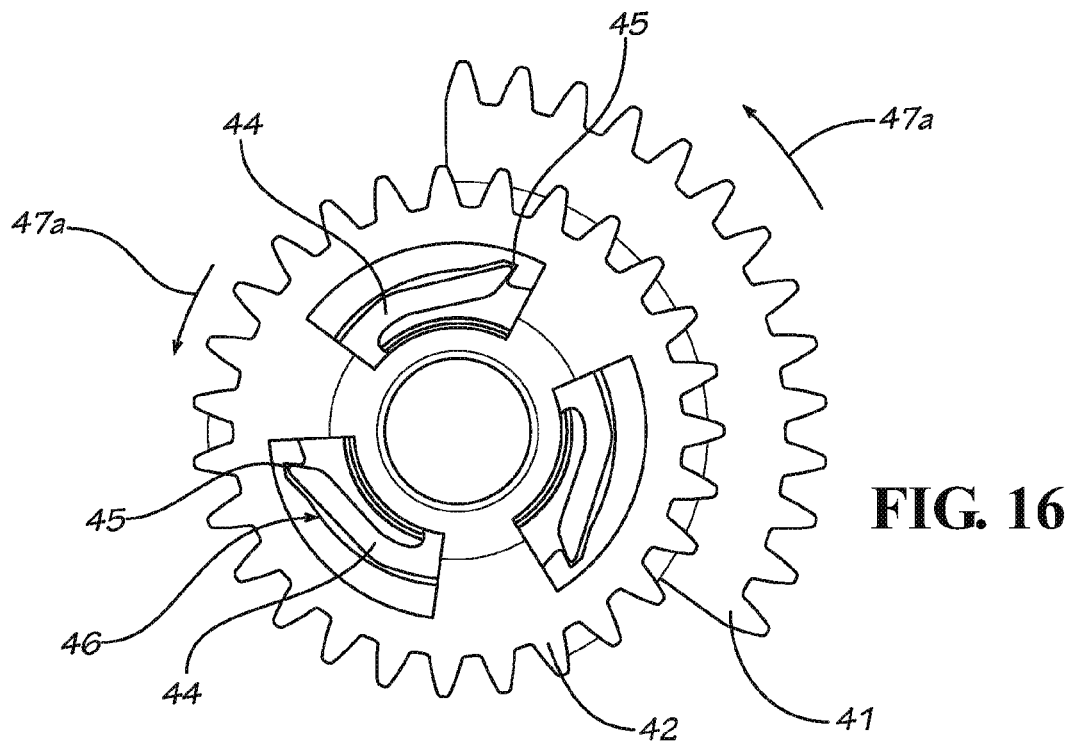
FIG. 16 is a bottom view of the ratchet gear assembly of FIG. 11, showing the first ratchet gear rotating in a first angular direction and driving the second ratchet gear to rotate with it.
Figure 17:
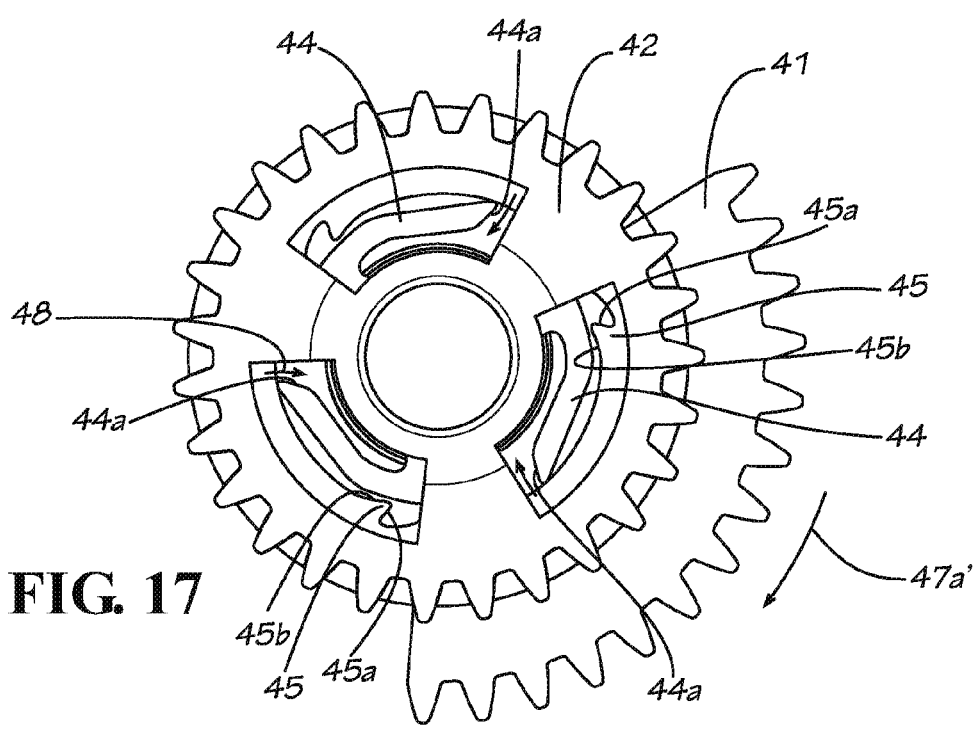
FIG. 17 shows the ratchet gear assembly of FIG. 16, with the first ratchet gear rotating in a second opposite angular direction while the second ratchet gear is held stationary.
Figure 18:
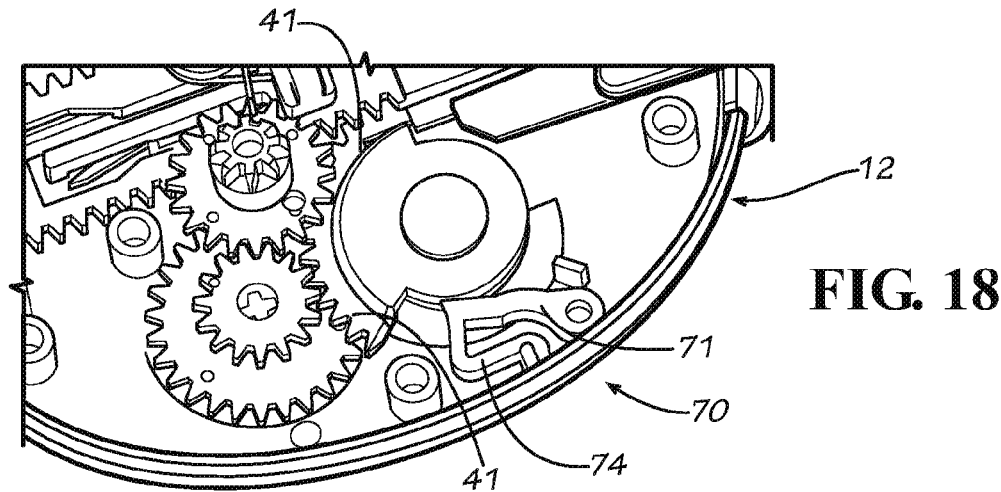
FIG. 18 is a top perspective view of a portion of the lancing device of FIG. 1, with the housing top and the housing bottom internal cover removed to reveal the internal advancement mechanism, and with the second ratchet gear not shown for clarity of illustration.

In operation, the catch surfaces 44a of the resilient arms 44 are contacted and held by the catch surfaces 45a of the ratchet teeth 45 when the first gear 41 is rotated in the first direction. Thus, as shown in FIG. 16, when the first gear 41 is rotationally driven in the first direction, the catch surfaces 44a of the resilient arms 44 of the second gear 42 are engaged by corresponding ones of the catch surfaces 45a of the ratchet teeth 45 of the first gear to rotationally drive the second gear to rotate with it (as indicated by angular directional arrows 47a). But when the first gear 41 is rotated in the second opposite direction, the resilient arms 44 resiliently deflect and bypass the ratchet teeth 45. Thus, as shown in FIG. 17, when the first gear 41 is rotationally driven in the second opposite direction (as indicated by angular directional arrow 47a'), the catch surfaces 45a of the ratchet teeth 45 are rotated out of engagement with the catch surfaces 44a of the resilient arms 44 so that the second drive gear 42 is not engaged and driven to rotate along with the first drive gear. Then as the first gear 41 is rotated further in the second direction, the resilient arms 44 are resiliently deflected radially inward (as indicated by the radial directional arrows 48) by engagement with the ramped surfaces 45b so that the arms bypass the next tooth 45 until the arms resiliently return to their engaged positions with their catch surfaces 44a again in direct opposition to the catch surfaces 45 of the next teeth.

In an alternative embodiment, the inter-gear ratcheting drive assembly includes two or another number of pawls and teeth. In yet another alternative embodiment, the ratcheting drive assembly includes one pawl and a plurality of teeth. In still another alternative embodiment, the ratcheting drive assembly includes at least one pawl extending from the first drive gear and at least one tooth formed by the second drive gear (a "vice versa" arrangement). In yet still another alternative embodiment, the ratcheting drive assembly includes at least one pivotal, spring-biased, rigid-arm pawl instead of the described resilient-arm pawl.

In another alternative embodiment of the ratcheting drive assembly, the catch surfaces are defined by detent elements of the first and second gears. Thus, the pawl is provided by a detent defining a catch surface, the tooth is provided by a detent defining a catch surface, and the ramped disengagement surface is defined by the first or second gear adjacent one of the detent lock surfaces. For example, the pawl and tooth detent elements can be provided by mating male and female elements each quarter-spherically shaped (i.e., one symmetrical half of a dome), with opposing flat surfaces defining the catch surfaces and with the curved surface defining the ramped disengagement surface. The pawl detents can be resiliently deflectable, spring biased, or otherwise configured to move between engaged and disengaged positions.

And in yet still other alternative embodiments, the inter-gear unidirectional drive assembly is not provided by a ratchet assembly but rather by a free-wheel mechanism or a clutch mechanism.

In order to secure the second drive gear 42 stationary (i.e., against co-rotation with the first drive gear 41 in the second direction 47a') when the first gear is rotating in the second direction, the second-gear unidirectional lock assembly is provided. In particular, the second-gear unidirectional drive assembly includes at least one lock surface defined by or extending from a retainer element (e.g., mounted to, extending from, or formed into a sidewall of the housing 12) and a lock element of the second drive gear 42. The lock surfaces are each engaged to lock the second gear from co-rotating with the first gear in the second direction, with at least one of the lock surfaces not engaged when the first gear rotates in the first direction. Such disengagement can be caused by at least one disengagement surface that moves at least the retainer element, which defines at least one of the lock surfaces.

For example, the second-gear unidirectional lock assembly can be provided by a second-gear ratcheting lock assembly including at least one pawl retainer element and at least one tooth element that is operably engaged by the pawl retainer. The pawl retainer can extend from one of the second drive gear and the housing (directly, or indirectly via an intermediate structure), and the tooth can extend from the other one of the second drive gear and the housing. The pawl retainer defines one of the lock surfaces and the tooth defines the other one of the lock surfaces. One or more ramped disengagement surfaces are defined by the pawl retainer and/or the tooth and are positioned adjacent that lock surface. The ramped disengagement surface(s) can be linear, curved, or a combination thereof.

In operation, the lock surfaces oppose each other so that, when the first drive gear is rotated in the second direction, with the second drive gear not driven in co-rotation with it, the pawl retainer lock surface contacts the tooth lock surface to secure the second gear in place. But when the first gear is rotated in the first direction, the tooth lock surface is rotated away from the retainer lock surface, so the second gear is not restrained from being rotationally driven by the first gear. And when the first gear is rotated further in the first direction, the ramped surface is engaged by the pawl to temporarily displace (from the engaged to the disengaged position) the pawl and its lock surface so that the tooth lock surface rotates past the pawl lock surface. Once the ramped surface has been cleared, the pawl returns to the engaged position so that the lock surfaces are again in an opposing relationship with each other so that when the first gear is again rotated in the second direction the second gear is locked from co-rotating with it.

In the ratcheting lock assembly 70 of the depicted embodiment (see FIGS. 10 and 18-20), the at least one pawl retainer is provided by a single pawl arm 71 that is pivotally mounted to and extends inwardly from the housing 12 at its outer periphery. And the at least one tooth is provided by three ratchet lock teeth 43 extending from the second drive gear 42. The ratchet lock teeth 43 include lock surfaces 49 (see also FIG. 15), and the pawl 71 includes a lock surface 73 and a ramped disengagement surface 72. The ratchet lock teeth 43 can be positioned, for example, on a top surface of the second gear 42. The ratchet lock teeth 43 can be made as integral features of, or separate structures coupled to, the second gear 42. The ratchet lock teeth 43 are preferably separate structures from the gear teeth of the second gear 42 (in the depicted embodiment, the ratchet teeth and the gear teeth are positioned along coaxial circles with different radii and in different rotational planes, with the ratchet teeth not designed for gear-meshing in a gear train). In addition, a spring 74, such as the depicted leaf-spring arm, extends between and biases against the pawl arm 71 and the housing 12 to urge the pawl arm into an engaged position engaging the ratchet lock teeth 43 when not displaced to a disengaged position by the ramped disengagement surface 72. The leaf-spring arm 74 can be made as an integral feature of, or a separate structure coupled to, the pawl arm 71.

Figure 19:
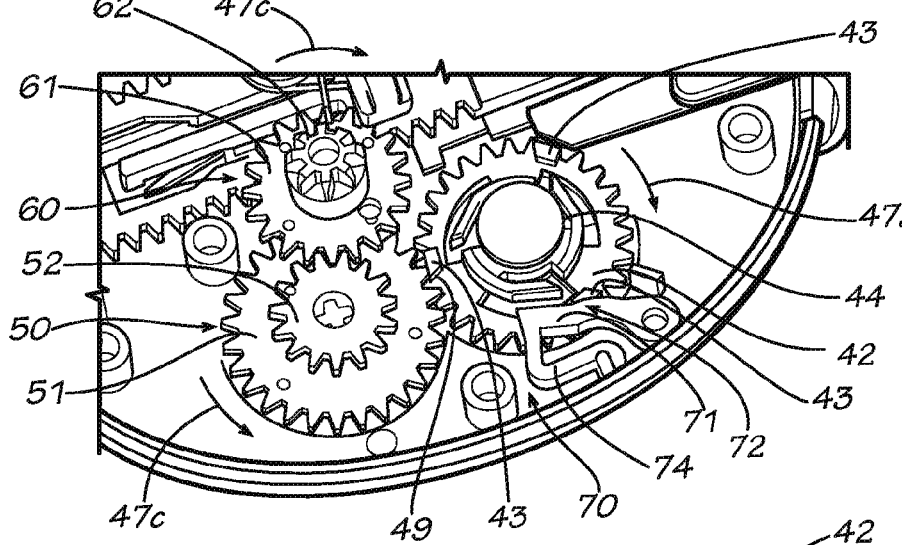
FIG. 19 shows the lancing device portion of FIG. 18, with the first ratchet gear removed to reveal the underlying second gear, which is rotating in the first angular direction.
Figure 20:
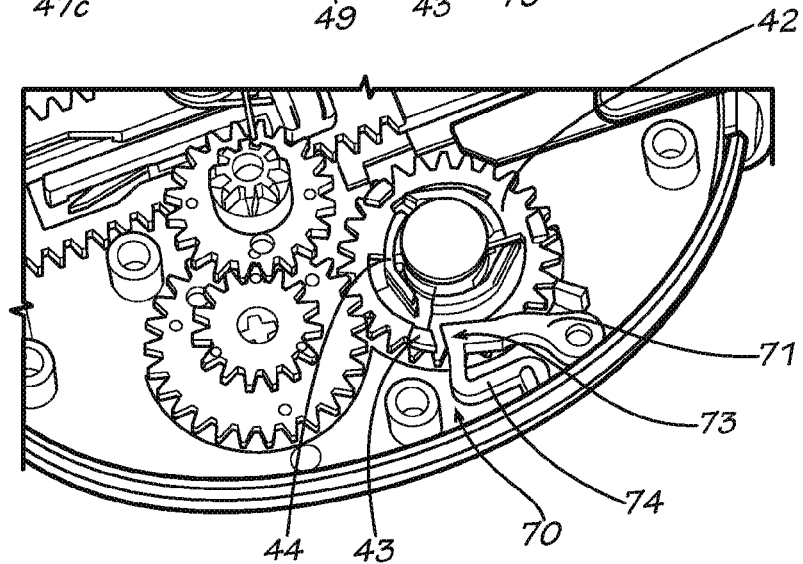
FIG. 20 shows the lancing device portion of FIG. 19, with the second gear locked from rotating in the second opposite angular direction.

In operation, one of the ratchet lock teeth 43 rotates across the ramped surface 72 of the pawl arm 71 to push the pawl arm from the engaged position to the disengaged position when the second gear 42 is rotated in the first direction 47a.Thus, as shown in FIG. 19, when the second gear 42 rotates in the first direction 47a, that ratchet lock tooth 43 is able to bypass the pawl 71 by ramping along the ramped surface 72 of the pawl to pivot the pawl outwards against the spring action of the leaf spring arm 71 against the housing 12. But, after that ratchet lock tooth 43 has cleared the pawl 71 and the pawl has returned to its engaged position, the lock surface 49 of that ratchet lock tooth directly opposes and engages the lock surface 73 of the pawl arm. Thus, as shown in FIG. 20, the second drive gear 42 is prevented from rotating in the second direction once the lock surface 49 of that ratchet lock tooth 43 opposes and engages the lock surface 73 of the pawl arm 71 when the pawl arm is in the engaged position and biased there by the leaf-spring arm 74. Then as the second gear 42 is again rotated in the first direction 47a with the first gear 41, the next one of the ratchet lock teeth 43 rotates across the ramped surface 72 of the pawl 71 to again push the pawl from the engaged position to the disengaged position so that next ratchet lock tooth bypasses the pawl.

In an alternative embodiment, the second-gear ratcheting lock assembly includes two or another number of pawls and teeth. In yet another alternative embodiment, the ratcheting lock assembly includes a plurality of pawls and a plurality of teeth. In still another alternative embodiment, the ratcheting lock assembly includes at least one pawl extending from the second ratchet gear and at least one tooth formed by the housing (a "vice versa" arrangement). In yet still another alternative embodiment, the ratcheting lock assembly includes at least one resilient, flexible-arm pawl instead of the described spring-biased pawl.

In another alternative embodiment of the ratcheting lock assembly, the lock surfaces are defined by detent elements of the retainer and the second gear. Thus, the pawl is provided by a detent defining a catch surface, the tooth is provided by a detent defining a catch surface, and the ramped disengagement surface is defined by the pawl or the second gear adjacent one of the detent lock surfaces. For example, the pawl and tooth detent elements can be provided by mating male and female elements each quarter-spherically shaped (i.e., one symmetrical half of a dome), with opposing flat surfaces defining the catch surfaces and with the curved surface defining the ramped disengagement surface. The pawl detents can be resiliently deflectable, spring biased, or otherwise configured to move between engaged and disengaged positions.

In still another alternative embodiment, the second-gear unidirectional lock assembly engages and restrains from reverse rotation one of the intermediate/idler or pinion gears, instead of the second drive gear directly. These gears are enmeshed with each other in the gear train, so preventing reverse rotation of them will thereby indirectly prevent reverse rotation of the second drive gear.

And in yet still other alternative embodiments, the second-gear unidirectional lock assembly is not provided by a ratchet assembly but rather by incorporating fixed detents on the housing or another non-rotating component that engage with mating features on a gear. The gear is provided with a spring element acting along the axis of the spring tending to push the gear against the fixed detents of the housing. As the gear rotates in one direction it has a ramp on one or both of the parts that cause it to shift axially against the spring. In the opposite direction, no ramp is provided. In still other alternative embodiments, the second-gear unidirectional lock assembly is provided by free-wheel mechanism or a clutch mechanism.

Referring still to FIGS. 10 and 18-20, the intermediate idler gear assembly 50 includes a first input gear 51 and second output gear 52 rotationally mounted about the same axis and interconnected so that they rotate in sync with one another. For example, the first and second intermediate gears 51 and 52 can be integrally formed (e.g., of molded plastic) as a single piece. The first intermediate gear 51 is engaged and rotationally driven in angular direction 47b by the second ratchet gear 42 when the second ratchet gear rotates in the angular direction 47a.

The pinion gear assembly 60 includes a first input gear 61 and a second output gear 62 rotationally mounted about the same axis and interconnected so that they rotate in sync with one another. For example, the first and second pinion gears 61 and 62 can be integrally formed (e.g., of molded plastic) as a single piece. The first pinion gear 61 is engaged and rotationally driven in angular direction 47c by the second intermediate gear 52 when the second intermediate gear rotates in the angular direction 47b. The second pinion gear 62 engages and rotationally drives a cartridge gear to sequentially advance the lancets into the active position for use, as described in more detail below.

The resultant gear train between the rack 22, the ratchet gear assembly 40, the intermediate gear assembly 50, and the cartridge pinion gear assembly 60 defines the general rotation transmission of the ratcheting advancement mechanism 30. The intermediate idler gear assembly 50 provides a gear ratio to produce the desired revolutions of the second pinion gear 62 based on the translating movement of the rack gear 22, thereby enabling the housing 12 to be designed and dimensioned in a relatively small size.

In an alternative embodiment, the intermediate gear assembly is not included in the advancement assembly 30 and the second ratchet gear directly engages and rotationally drives the first pinion gear. In another alternative embodiment, the pinion gear assembly 60 includes only one pinion gear, which is rotationally driven by the second ratchet gear (directly or indirectly by one or more intermediate idler gears) and which in turn engages and rotationally drives the cartridge gear. And in yet another alternative embodiment, the pinion gear assembly 60 is not included and the second ratchet gear itself acts as the pinion gear that engages and rotationally drives the cartridge gear.

In further alternate embodiments, the ratcheting advancement mechanism 30 is adapted to allow the second pinion gear 62 to rotate when the grip 20 of the operating handle 21 is pushed inwards and to prevent the second pinion gear from rotating when the grip 20 is pulled outwards (a "vice versa" arrangement). The advancement mechanism 30 can alternatively be designed to rotate the second pinion gear 62 upon every push and pull of the grip 20 inwards and outwards from the housing 12. The numbers, positions, shapes, and dimensions of the gears and other components of the ratcheting advancement mechanism 30 can differ based on the size of the lancing device housing 12 that the advancement mechanism 30 is to be used within or the amount of angular rotation desired from the second pinion gear 62. Thus, while in the depicted embodiment each pull/push operation of the operating handle 20 rotates the second ratchet gear 42 by ⅓ (120 degrees), in alternative embodiments the second ratchet gear is thereby rotated by a different angular amount.

Figure 21:
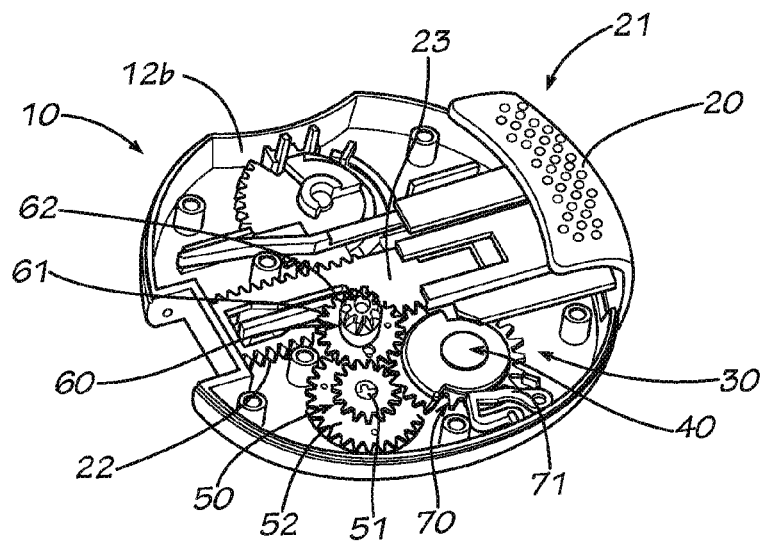
FIG. 21 is a top perspective view of the lancing device of FIG. 1, with the housing top and the housing bottom cover removed to reveal the internal advancement mechanism and with the operating handle in the retracted position.
Figure 22:
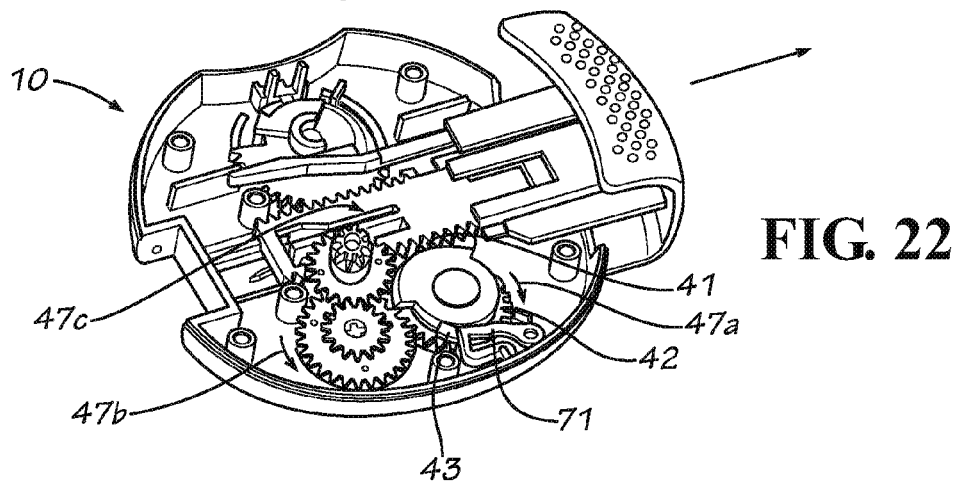
FIG. 22 shows the lancing device of FIG. 21, with the operating handle moving through an intermediate position to operate the advancement mechanism.
Figure 23:
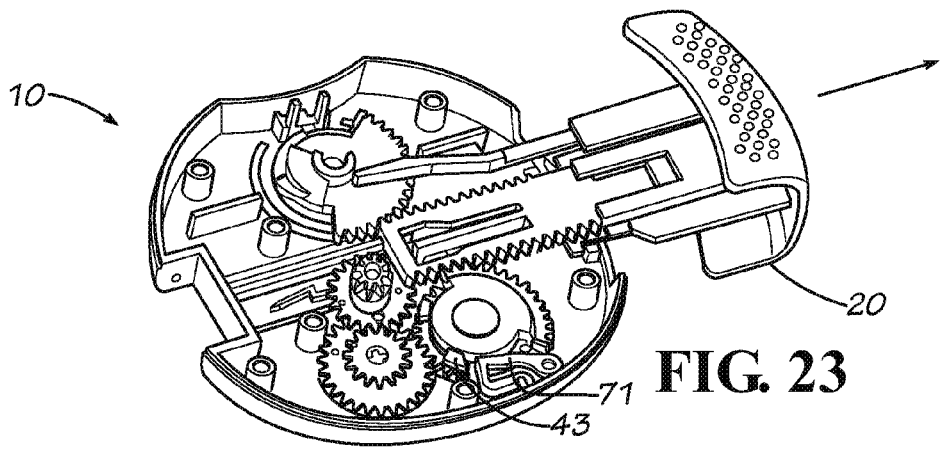
FIG. 23 shows the lancing device of FIG. 21, with the operating handle in the extended position.

Having described structural details of the advancement mechanism 30, its operation will now be described with reference to FIGS. 21-26. As shown in FIG. 21, the lancing device is stored when not in use with the operating handle 21 in the retracted position. FIG. 22 shows the operating handle 21 being moved (as indicated by the linear directional arrow) through an intermediate position to operate the advancement mechanism 30. Thus, the rack gear 22 rotationally drives the drive gear assembly 40 in the direction 47a, which rotationally drives the intermediate idler gear assembly 50 in the direction 47b, which rotationally drives the pinion gear assembly 60 in the direction 47c. The first and second gears 41 and 42 of the drive gear assembly 40 both rotate in the direction 47a by the operation of the inter-gear unidirectional ratcheting drive assembly 46, which transmits the rotation of the first gear to the second gear so they co-rotate in sync. FIG. 23 shows the lancing device 10 with the operating handle 21 pulled all the way to the fully extended position. This completes the "pull" portion of one "push/pull" operational cycle.

Figure 24:
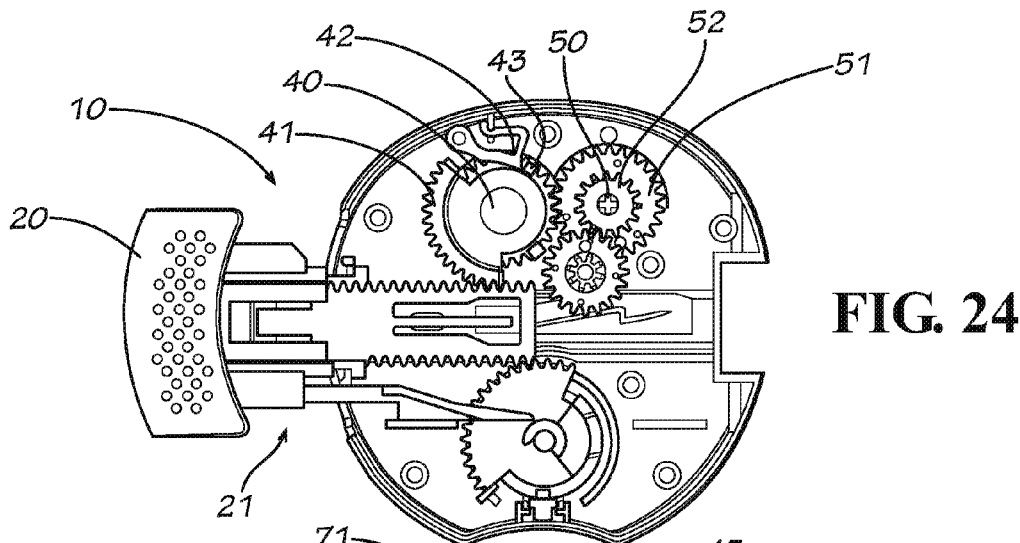
FIG. 24 is a top view of the lancing device of FIG. 23.
Figure 25:
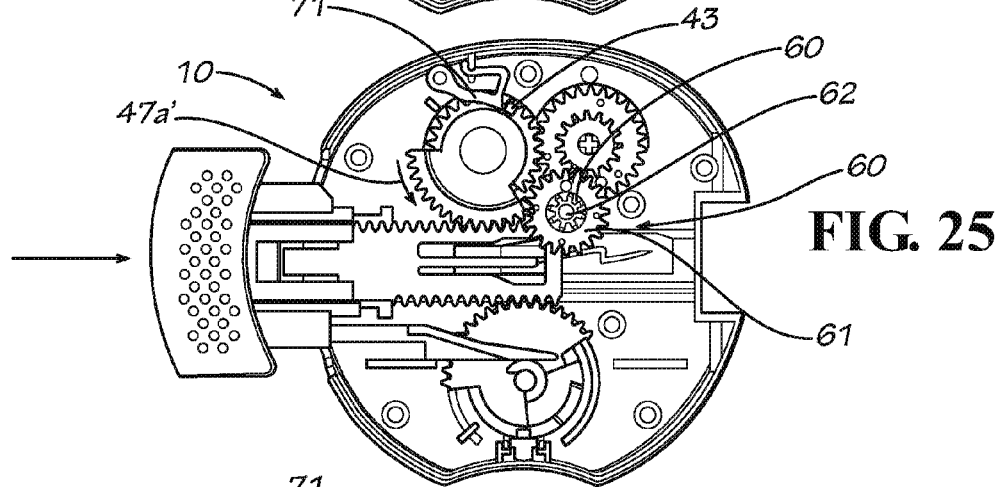
FIG. 25 is a top view of the lancing device of FIG. 24, with the operating handle moving back through the intermediate position to reset the advancement mechanism.
Figure 26:
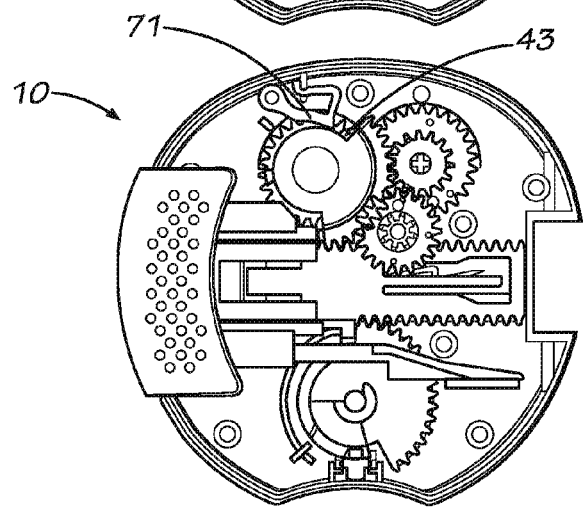
FIG. 26 is a top view of the cartridge-based lancing of FIG. 24, with the operating handle moved back to the retracted position.
Figure 27:
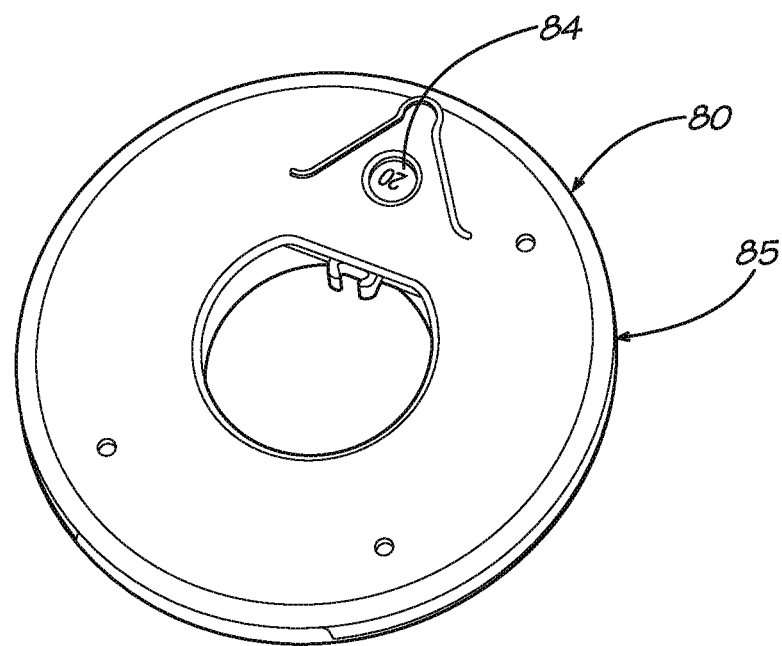
FIG. 27 is a top perspective view of a lancet cartridge used with the lancing device of FIG. 1.
Figure 28:
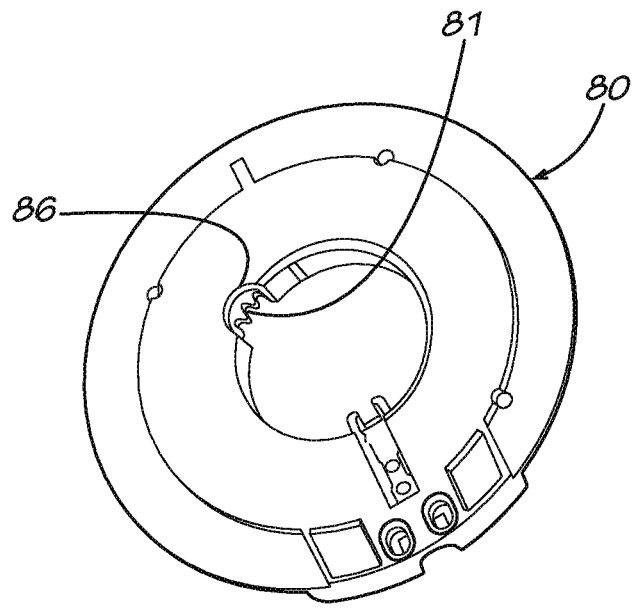
FIG. 28 is a bottom perspective view of the lancet cartridge of FIG. 27.
Figure 29:
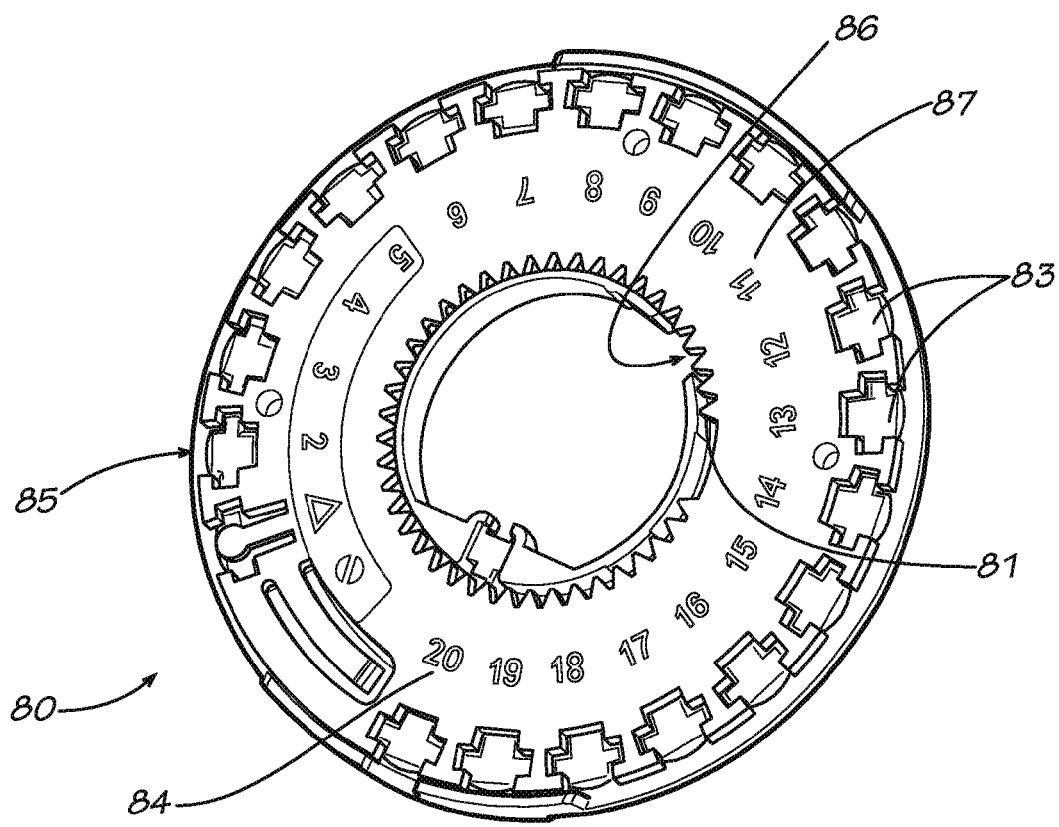
FIG. 29 is a top perspective view of the lancet cartridge of FIG. 27, with the cartridge housing top removed to reveal the internal lancets.
Figure 30:
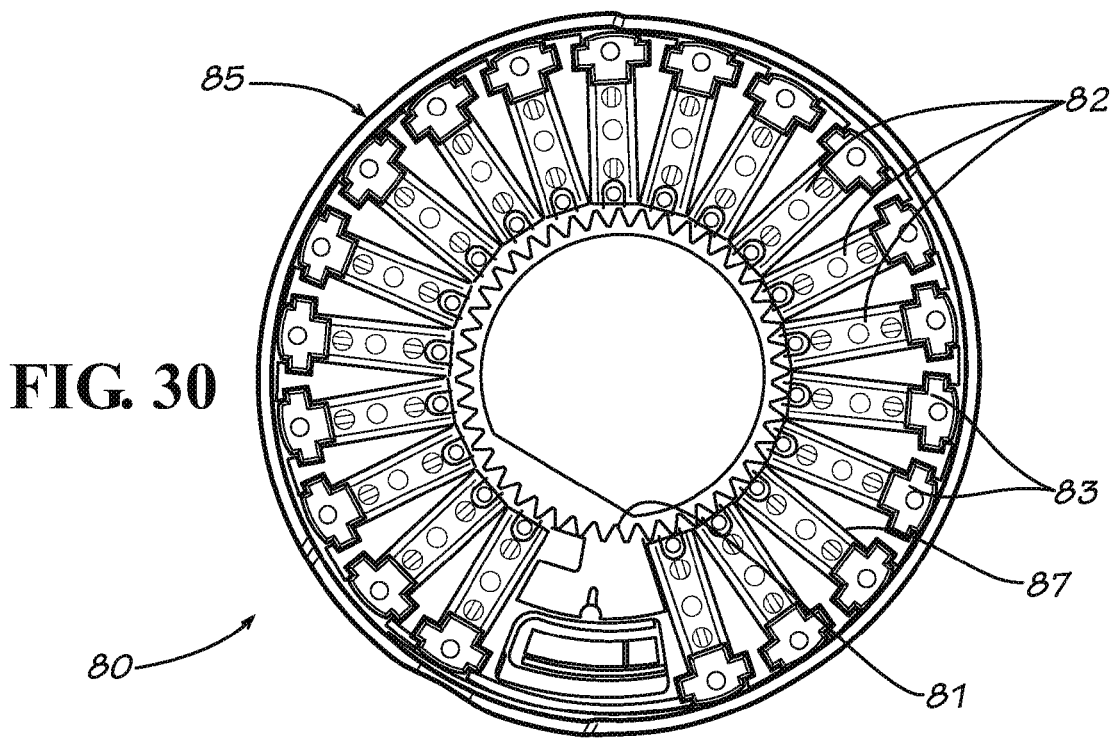
FIG. 30 is a bottom view of the lancet cartridge of FIG. 27, with the cartridge housing bottom removed to reveal the internal lancets.
Figure 31:
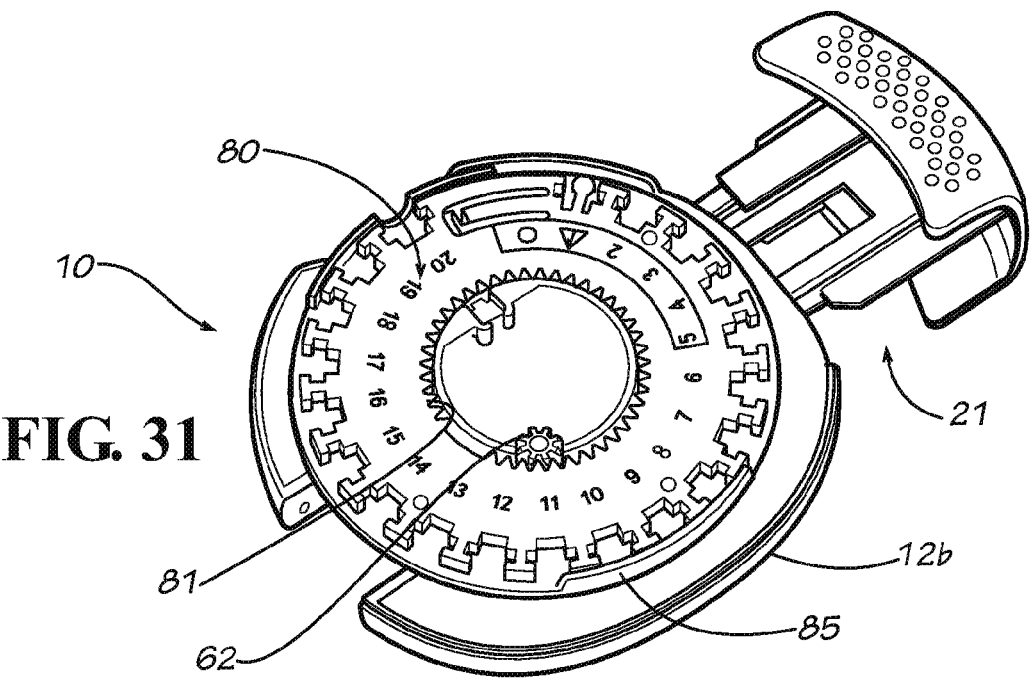
FIG. 31 is a top perspective view of the lancet cartridge of FIG. 27 mounted to the lancing device of FIG. 1, with the cartridge housing top removed to show the engagement of the cartridge by the ratcheting mechanism of the lancing device.
Figure 32:
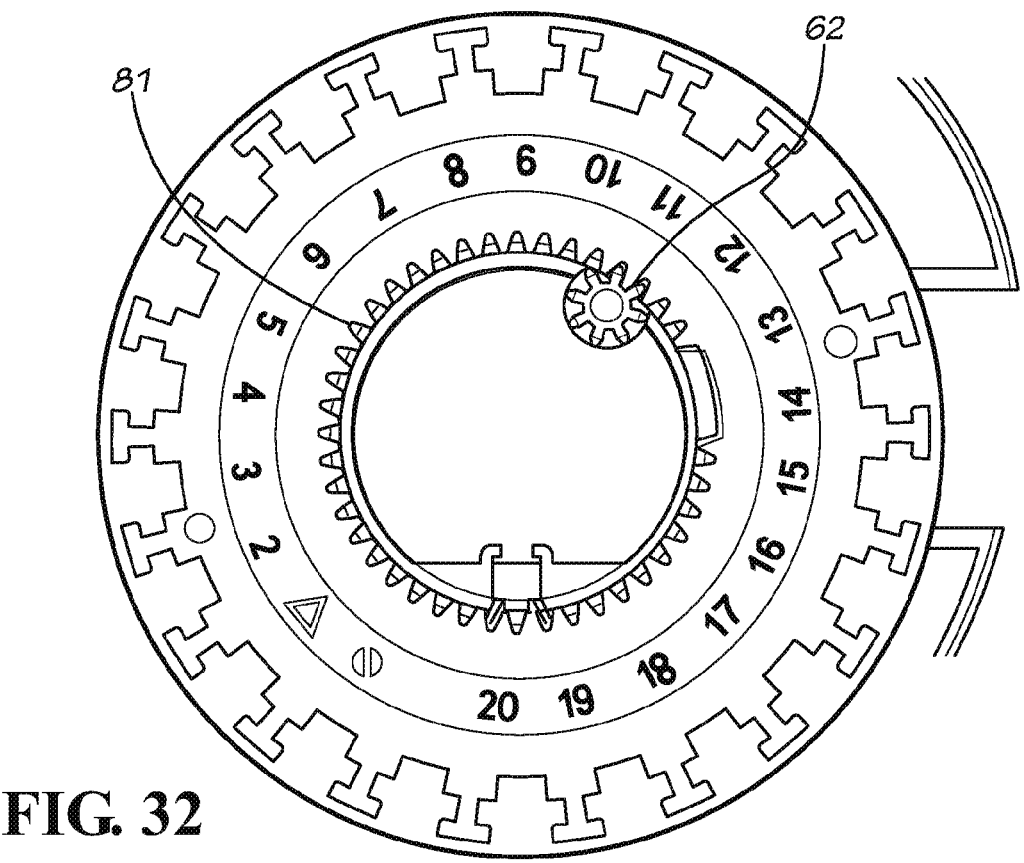
FIG. 32 is a plan view of a portion of the lancet cartridge and the lancing device of FIG. 31.
Figure 33:
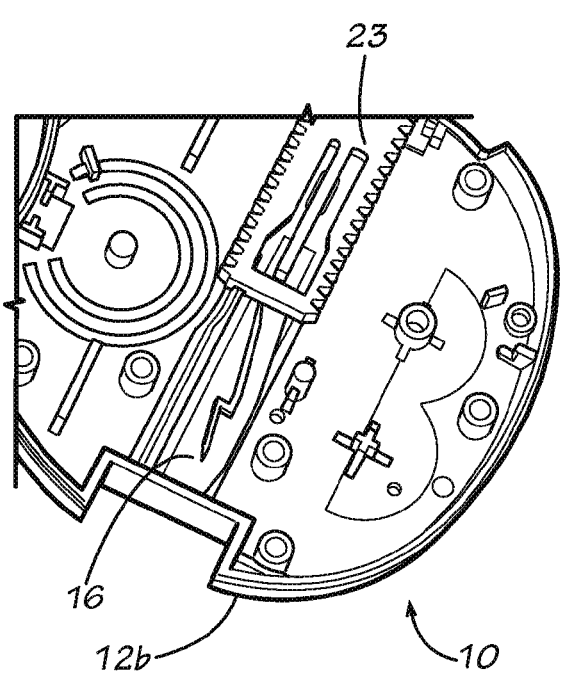
FIG. 33 is a top perspective view of a portion of the lancing device of FIG. 1, with the housing top and the housing main bottom cover removed to reveal the internal charging mechanism, and with the operating handle in the extended position, showing a portion of the charging mechanism (with all rotary gears removed for clarity).
Figure 34:
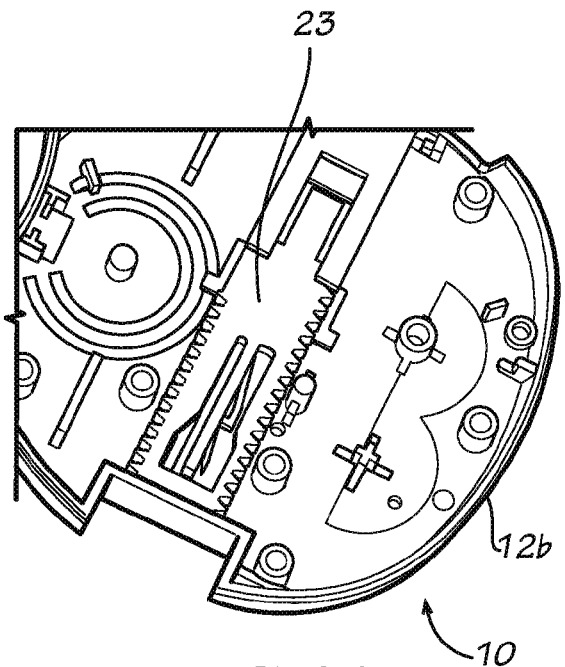
FIG. 34 shows the lancing device portion of FIG. 33 with the operating handle in the retracted position.
Figure 35:
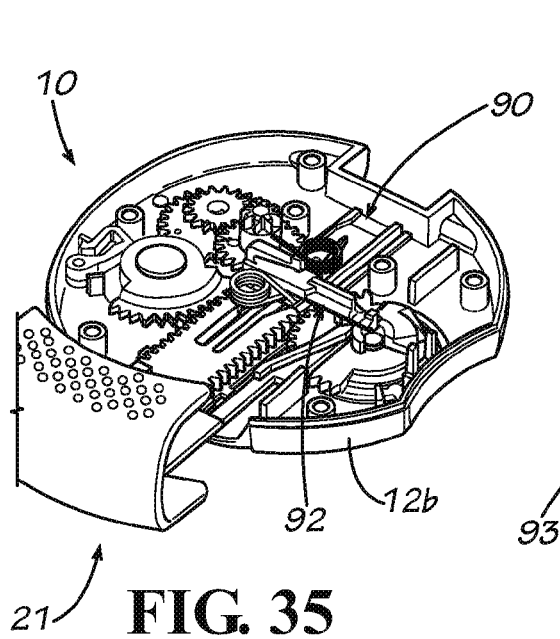
FIG. 35 is another top perspective view of the lancing device of FIG. 33.
Figure 36:
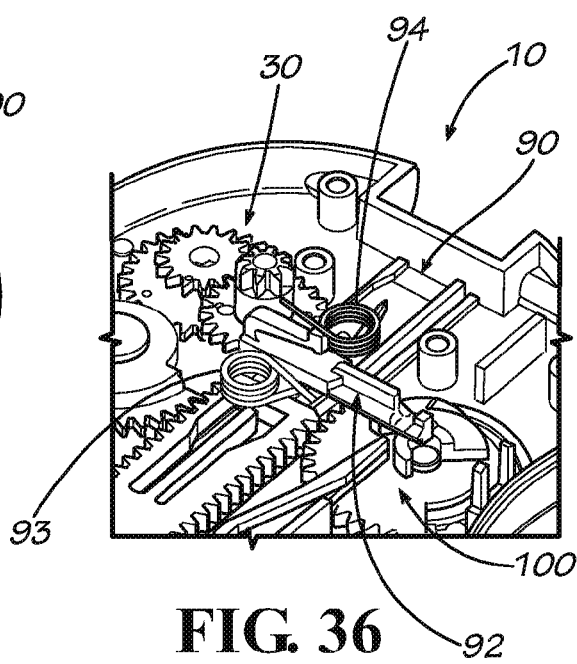
FIG. 36 shows a blown-up detail view of a portion of the lancing device of FIG. 35.
Figure 37:
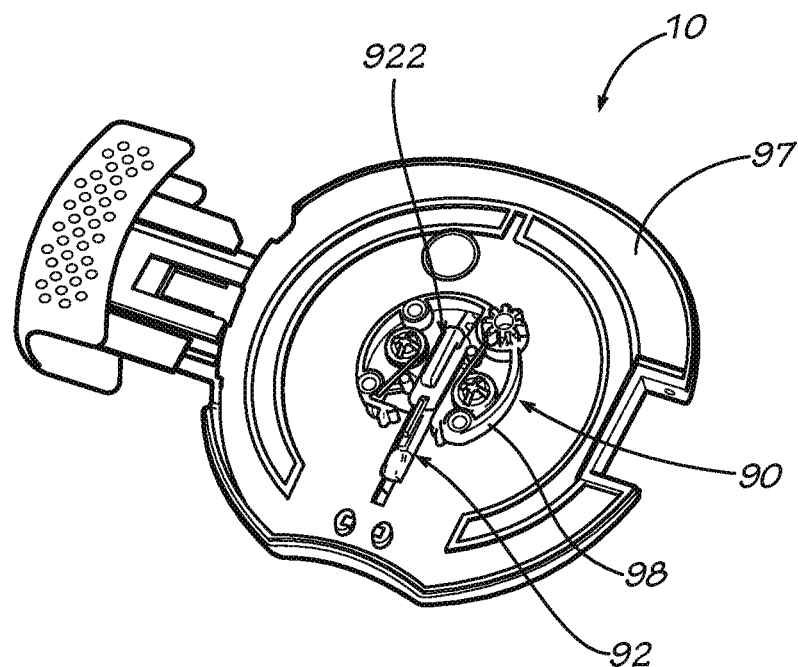
FIG. 37 is another top perspective view of the lancing device of FIG. 35, with the housing top removed but not the housing bottom main cover.
Figure 38:
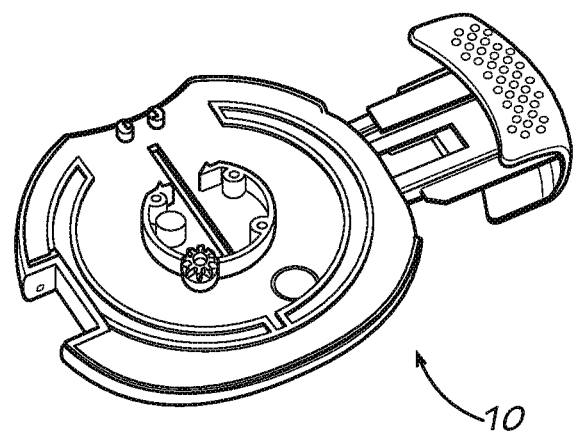
FIG. 38 is another top perspective view of the lancing device of FIG. 37, with the housing bottom piston cover in place.
Figure 39:
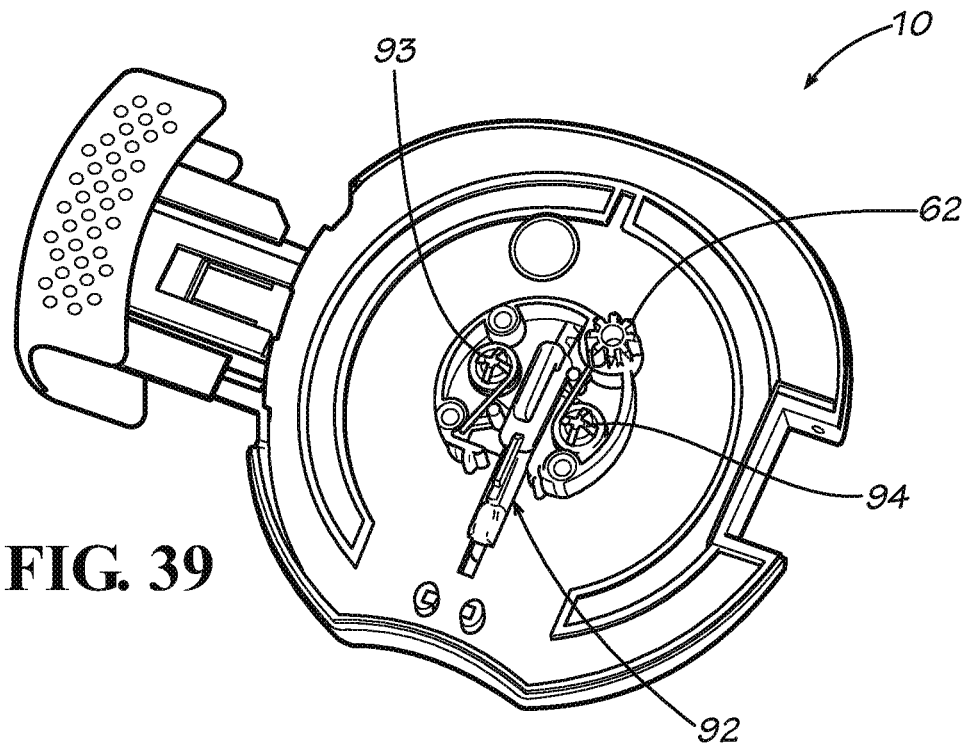
FIG. 39 is a blown-up view of the lancing device of FIG. 37.
Figure 40:
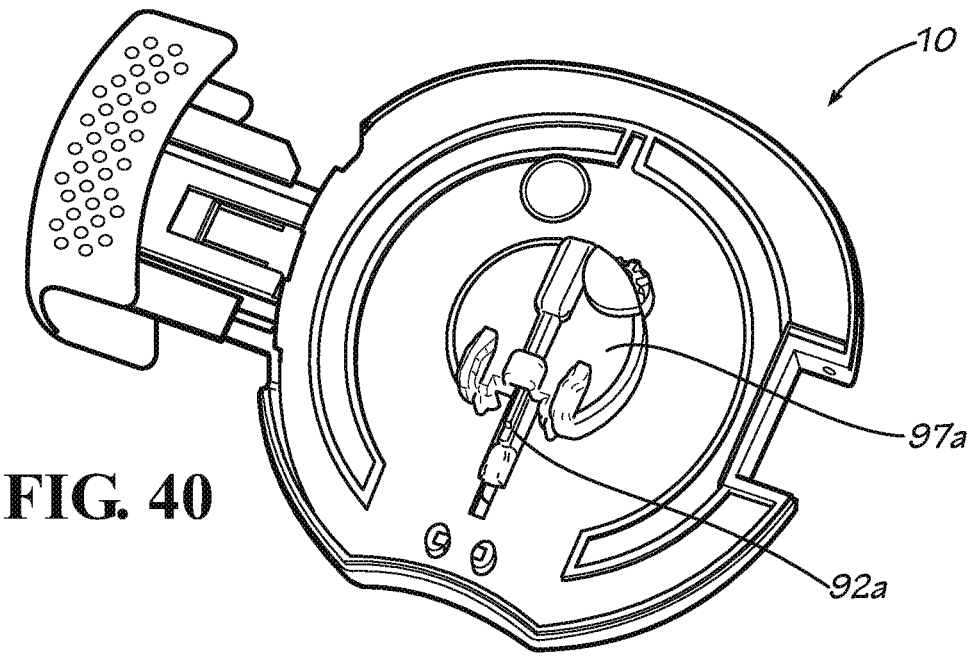
FIG. 40 is another view, blown up, of the lancing device of FIG. 38, with the housing bottom piston cover in place.
Figure 41:
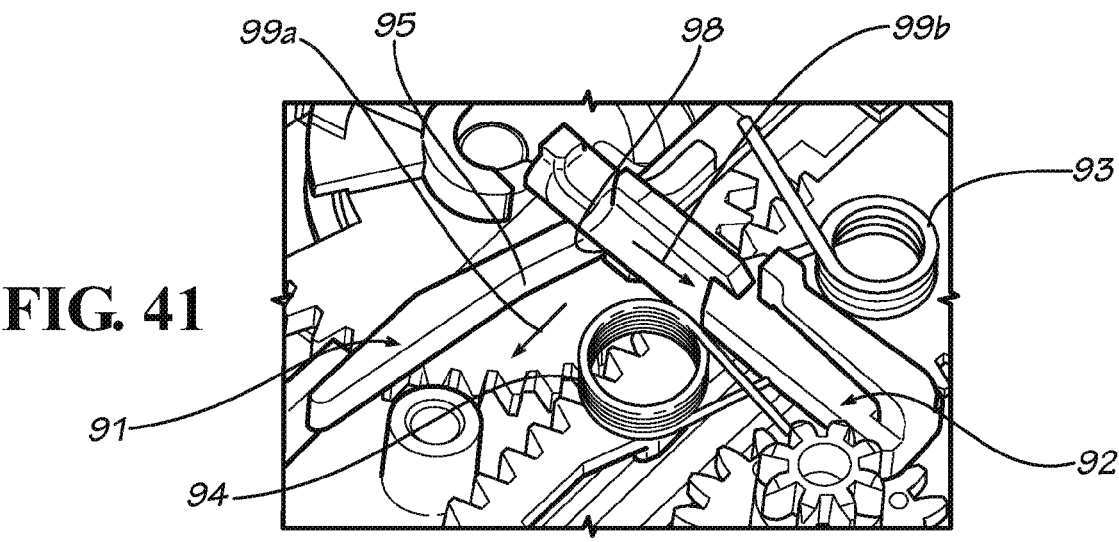
FIG. 41 is a detail view, further blown-up, of the lancing device portion of FIG. 36, showing the lancet being retracted to its charged/retracted position.
Figure 42:
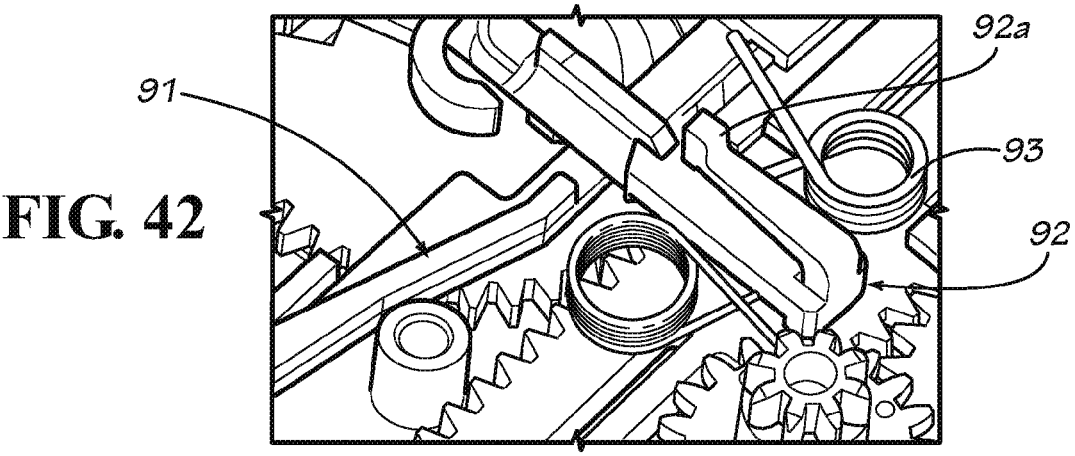
FIG. 42 shows the lancing device portion of FIG. 41, with the lancet being driven through its lancing stroke.
Figure 43:
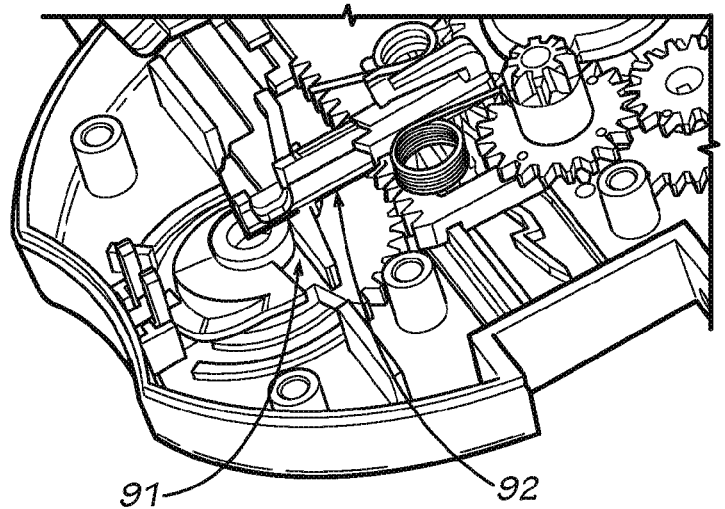
FIG. 43 is another top perspective view of the lancing device portion of FIG. 42.
Figure 44:
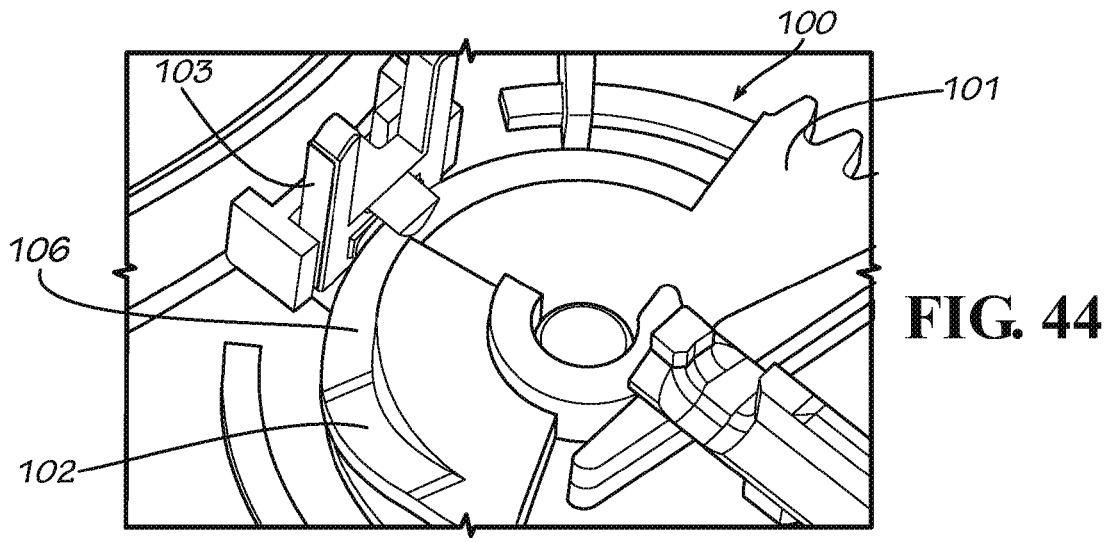
FIG. 44 is a top perspective view of a portion of the lancing device of FIG. 1, with the housing top and the housing main bottom cover removed to reveal the internal cap-displacement mechanism.
Figure 45:
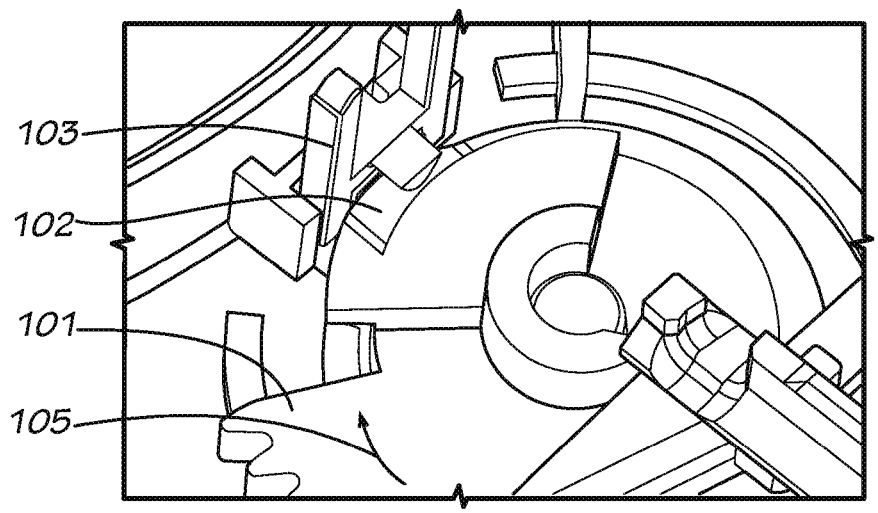
FIG. 45 shows the lancing device portion of FIG. 44 with the cap-displacement mechanism being operated to displace the cap of the active lancet from the lancing stroke path.
Figure 46:
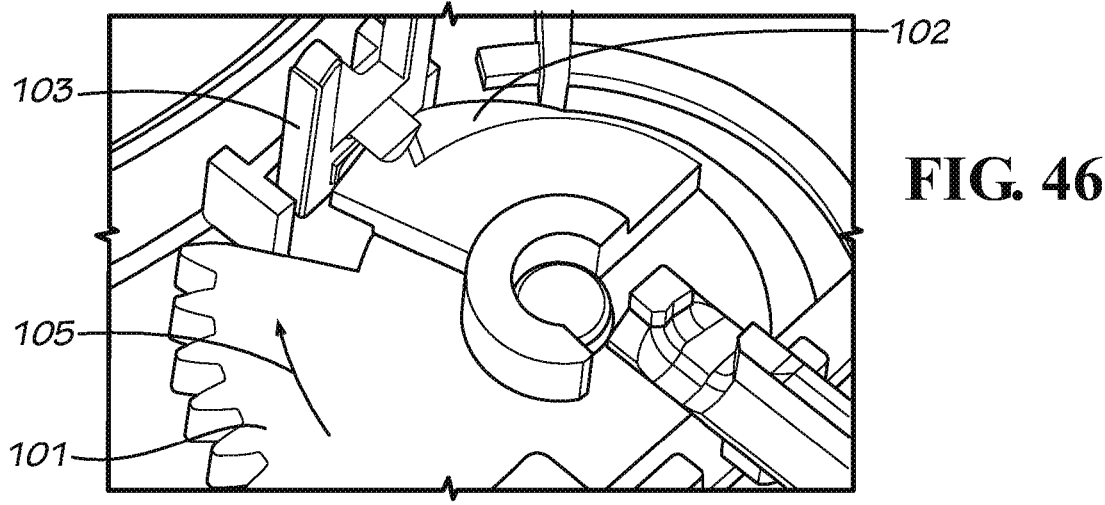
FIG. 46 shows the lancing device portion of FIG. 44 with the cap-displacement mechanism being fully operated to fully displace the cap of the active lancet.

FIG. 24 shows the lancing device 10 in the same condition as in FIG. 23. As shown in FIG. 25, the operating handle 21 is moved back through the intermediate position to reset the advancement mechanism 30 for subsequent use. Thus, the rack gear 22 rotationally drives the first gear 41 of the drive gear assembly 40 in the opposite direction 47a'. But the second gear 42 of the drive gear assembly 40 is locked from co-rotation by the operation of the second-gear unidirectional ratcheting lock assembly 70. So the second gear 42 of the drive gear assembly 40 remains stationary. Because of this, the pinion gear assembly 50 also remains stationary, as necessarily does the intermediate idler gear assembly 50. Thus, the operating handle 21 is returned to its retracted position, without reversing the output pinion gear 62 (which would back up the just-used lancet to the active lancet position). FIG. 26 shows the lancing device 10 with the operating handle 21 pushed all the way back in to the fully retracted position. This completes the "push" portion of one "push/pull" operational cycle, with the advancement mechanism 30 now reset to advance a next lancet for use.

Referring now to FIGS. 27-32, the interrelationship between the advancement mechanism 30 and the cartridge assembly 80 will now be described. The cartridge 80 includes a housing 85 that holds a plurality of the lancets 82, for example, in a radial arrangement. The cartridge 80 includes a cartridge gear 81 that is engaged and rotationally driven by the pinion output gear 62 of the pinion gear assembly 60. In this way, when the advancement mechanism 30 is operated through one-half an operating cycle (e.g., by pulling the operating handle 21 from the retracted to the extended position), the pinion output gear 62 is rotationally driven. The pinion gear 62 then rotationally drives the cartridge gear 81 a certain indexed angular increment to advance a used one of the lancets 82 out of the active position and to advance a next fresh one of the lancets into the active position for use. The advancement mechanism 30 thereby allows the lancets 82 to be advanced accurately so that there will be no issues with jamming or misalignment caused by over- or under-advancement to the next sequential position.

In the depicted embodiment, the cartridge gear 81 is defined circumferentially along an outer circular wall of a circular carrier 87 that holds the lancets 82. The cartridge housing 85 is annular and includes a gear opening 86 in its inner circular wall through which the cartridge gear 81 on the internal carrier 87 is exposed for engagement by the pinion gear 62. So the pinion gear 62 engages the portion of the cartridge gear 81 of the carrier 87 that is exposed through the gear opening 86 of the cartridge housing 85 to rotate the carrier, thereby advancing the lancets 82 to their next sequential positions upon each indexed advancement of the carrier 87. The cartridge housing 85 is not rotated, only the internal carrier 87 and lancets 82 are. The carrier 87 can include lancet indicia 84 that are visible through an indicia opening in the cartridge housing 85 to provide a visible indication of how many lancets have been used or remain for use.

In an alternative embodiment, the cartridge gear is defined by the cartridge housing so that the cartridge housing, along with the lancets held within it, are all rotationally advanced. A carrier is not needed in this embodiment. In yet another alternative embodiment, the cartridge gear is cooperatively defined by all of the lancets, for example on their bodies (from which their lancing tips extend) or their sterility caps 83. The lancets can be still held by an internal carrier, which can also gearing between the lancets for a smooth advancing motion. In embodiments for using or dispensing items other than lancets, the advancement mechanism advances the items to the active position where they can be accessed, dispensed, deployed, implemented, etc., depending on the type of device.

In addition, the lancing device 10 can be designed to carry out other operations during the outward pull and/or inward push of the operating handle 20 relative to the housing 12, for example charging a drive mechanism, operating a de-capping mechanism, operating a cap-displacement mechanism, or operating other subassemblies of the overall lancing device. Having described the structure and operation of the advancement mechanism 30, details of other operational assemblies of the lancing device 10 of the depicted embodiment will now be described. It will be noted that the lancing device can be provided with only some of these additional assemblies, with other conventional assemblies for carrying out the same function provided or without any assemblies provided for carrying out these functions, as may be desired in a given application.

The depth adjustment mechanism 13 (see FIGS. 1-9) operates to provide adjustment for different puncturing depths of the lancet tip into the user's skin. The depth adjustment mechanism 13 can be of the type described and shown in detail in U.S. patent applications Ser. Nos. 12/522,764 and 12/522,765, both filed Jun. 30, 2009 (U.S. Patent Application Publications Nos. U.S. 2010/0094326 and U.S. 2010/0057119).

The actuation mechanism 16 (see FIG. 33) operates to release the active lancet 82 from the charged/retracted position so that it can be propelled by the discharging drive spring through its lancing stroke. The actuation mechanism can include a molded-in cantilever that pops up behind a bridge piece (e.g., made of plastic) when charged. When the actuation button 96 is pressed, it pushes the cantilever down allowing it to slide under the bridge.

Referring now to FIGS. 33-43, the charging mechanism 90 operates to retract an active-positioned lancet, charge a drive spring and, upon actuation of the actuation button, release the lancet to be propelled by the discharging drive spring through a lancing stroke. The charging mechanism 90 includes a guide element 91, a piston 92, a drive spring 93, a return spring 94, and an activation button 96 (see also FIG. 1). These components are located in the housing bottom 12b and, except for the lancet-engagement element 92a of the piston, concealed by a main cover panel 97 and a piston cover panel 97a. The guide 91 is a protrusion extending from the operating handle 21, for example, from the elongate member 23 that extends from the grip 20 and into the housing. The guide 91 includes a cam surface 95 that is engaged by a follower surface 98 of the piston so that when the follower travels along the cam surface the piston is retracted against the biasing force of the drive spring 93 to a charged position. In the depicted lancing device 10, the guide 91 is responsible for both arming the piston 92 and de-capping the lancets 82. The drive spring 93 and the return spring 94 can be provided as separate springs, as depicted, or by a single dual-function spring. And they can be provided by torsion springs, as depicted, or by other conventional types of springs such as coil springs (compression or tension), leaf springs, resilient members, or the like.

In operation, the operating handle 21 is pushed in toward the housing 12 to the retracted position, as indicated by the linear directional arrow 99a (see FIG. 41) (the "push" portion of the "push/pull" cycle, after the operating handle has been pulled out to the extended position to advance the lancets 82). When this is done, the cam surface 95 of the guide 91 engages and drives the follower 98—and thus the piston 92—back to a charged/retracted position, as indicated by the linear directional arrow 99b, where an actuation element of the piston is engaged by the activation button 96 to hold the piston in place. As the piston 92 is retracted against the spring force of the drive spring 93, the drive spring is charged such that it stores energy. The piston 92 is then released from engagement with the activation button 96 when the button is actuated (e.g., by being depressed). The piston 92 is then driven forward by the drive spring 93 through a lancing stroke until a puncturing tip of the active lancet 82 extends through a lancing opening in the housing 12. As the lancet 82 is propelled through its lancing stroke under the influence of the discharging drive spring, it biases against the return spring to store an energy charge in it. After the lancet 82 reaches the end of its forward travel, it is retracted into the housing 12 under the charge of the return spring.

Additional details of the structure and operation of this and similar charging mechanisms are disclosed in U.S. patent applications Ser. Nos. 12/522,764 and 12/522,765, both filed Jun. 30, 2009 (U.S. Patent Application Publications Nos. U.S. 2010/0094326 and U.S. 2010/0057119). It will be noted that the charging mechanism can include elements for actuating the active lancet in the retracted/charged position or a separate actuation mechanism can be provided.

Referring now to FIGS. 33-43, the cap-displacement mechanism 100 operates to remove the sterility caps 83 from the puncturing tips of the active-positioned lancet 82 before the lancing stroke. As the guide 91 of the charging mechanism 90 is moved into engagement with the piston 92 while the operating handle 21 is being pushed into the retracted position, a cap-displacement rack gear 104 of the operating handle engages and activates the cap-displacement mechanism 100. The cap-displacement rack gear 104 can be formed, for example, on the elongate member 23 that extends from the grip 20 and into the housing. In the depicted embodiment, the cap-displacement rack gear 104 is positioned on the elongate member 23 opposite the advancement rack gear 22. In alternative embodiments, a single rack gear drives both assemblies. And in still other embodiments, the cap-displacement mechanism 100 is actuated by another gear of another one of the operational assemblies of the lancing device, for example, by one of the idler gears of the advancement mechanism.

The cap-displacement mechanism 100 includes a lifter gear 101, a lifting ramp 102, and a lifter element 103. The lifter gear 101 can include gear teeth along its entire circumference or along only a portion of it, as depicted. The lifter gear 101 can be a dedicated rotary gear for use only in the cap-displacement mechanism 100, a shared gear also used in the charging mechanism, or a shared gear also used in the charging mechanism (e.g., one of the idler gears). The lifter gear 101 can include gear teeth along its entire circumference or along only a portion of it, as depicted. The lifting ramp 102 is formed on the lifter gear 101, for example, extending radially outward from its outer periphery, as depicted. The lifting ramp 102 defines an inclined surface that can be linear, curved, or a combination thereof. The lifting ramp 102 is positioned on the lifter gear 101 so that a pre-lifting surface 106 of the gear is traversed by the lifter 103 before it reaches the ramp for timing purposes. That is, the lifter 103 is not moved when the pre-lifting surface 106 of the lifting gear 101 is rotated through engagement with it. This allows the charging mechanism to retract the active lancet 82 and remove its cap 83 before the lifter 103 is moved to displace the removed cap. The lifter 103 includes a follower surface across which the lifting ramp 102 is rotated to axially displace the lifter. The lifter 103 also includes one (or more, e.g., two are depicted) fingers that engage the cap 83 of the active lancet 82 but that do not intrude into the lancing stroke path. Thus, the body of the lancet 82 can fit through the opening between the two depicted fingers of the lifter 103.

In operation, the cap-displacement rack gear 104 engages and rotationally drives the lifter gear 101 in angular direction 105 as the operating handle 21 is pushed in to the retracted position (the "push" portion of the "push/pull" cycle, after the operating handle 21 has been pulled out to the extended position to advance the lancets 82). As the lifter gear 101 is rotated in direction 105, its lifting ramp 102 is rotated into engagement with the lifter 103. The rotating inclined-surface lifting ramp 102 then pushes up the lifter 103 into engagement with the cap 83 of the active lancet 82. When the active lancet 82 is retracted to its charged/retracted position by the charging mechanism, the active lancet's cap 83 is held, for example by retaining elements, from retracting with the active lancet 82. So the displaced cap 83 remains in its original place and is thereby removed from its lancet 82. The lifter 103 then pushes the removed cap 83 out of the lancing stroke path. The displaced cap 83 can be held in its displaced position, for example, by cap-retaining elements of the cartridge 80. Alternatively, the cap 83 can be returned to its original position, for example, by a cap-return spring in the housing opposite the lifter. In any case, after the lancing device 10 has been actuated to fire the lancet 82, when the operating arm 21 is later pulled to its extended position to advance the now-used lancet 83 out of the active position, the cap-displacement gear 104 rotates the lifting gear 101 in the opposite angular direction. This rotates the lifting ramp 102 back to its original position, dropping the lifter 103 back down to its original position, ready to displace the cap 83 of the next lancet 82 advanced into the active position.

Additional details of the structure and operation of this and similar cap-displacement mechanisms are disclosed in U.S. patent applications Ser. Nos. 12/522,764 and 12/522,765, both filed Jun. 30, 2009 (U.S. Patent Application Publications Nos. U.S. 2010/0094326 and U.S. 2010/0057119). In particular, relevant details of lifters and lifting ramps are included in these disclosures.

Figure 47:
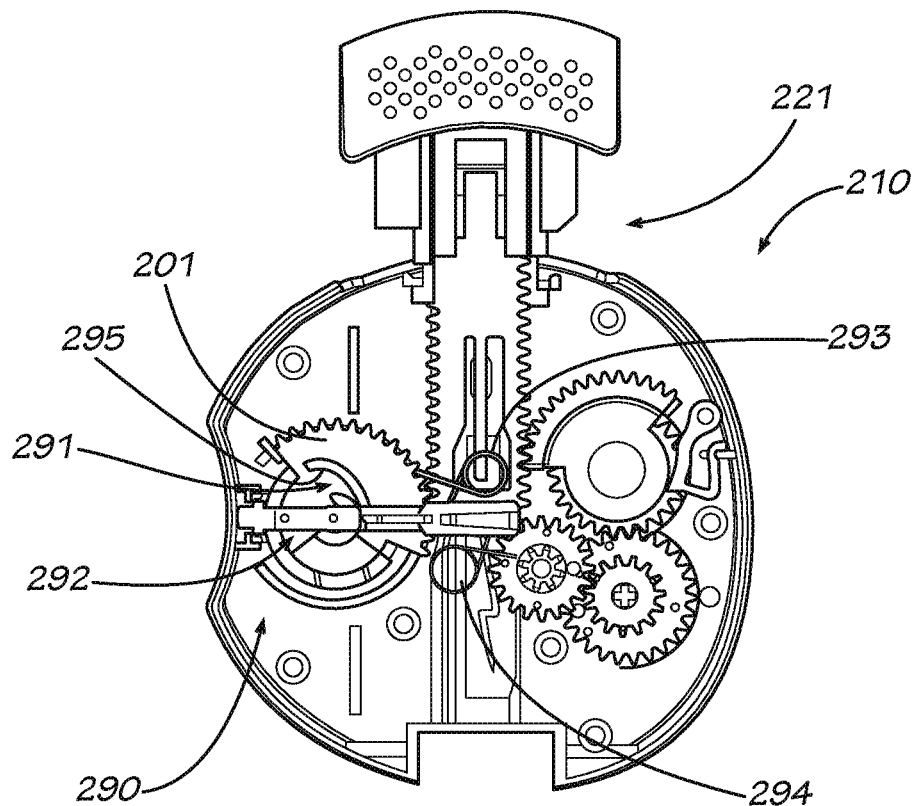
FIG. 47 is a plan view of a lancing device according to a second example embodiment of the present invention, showing a charging mechanism with a rotary pawl.
Figure 48:
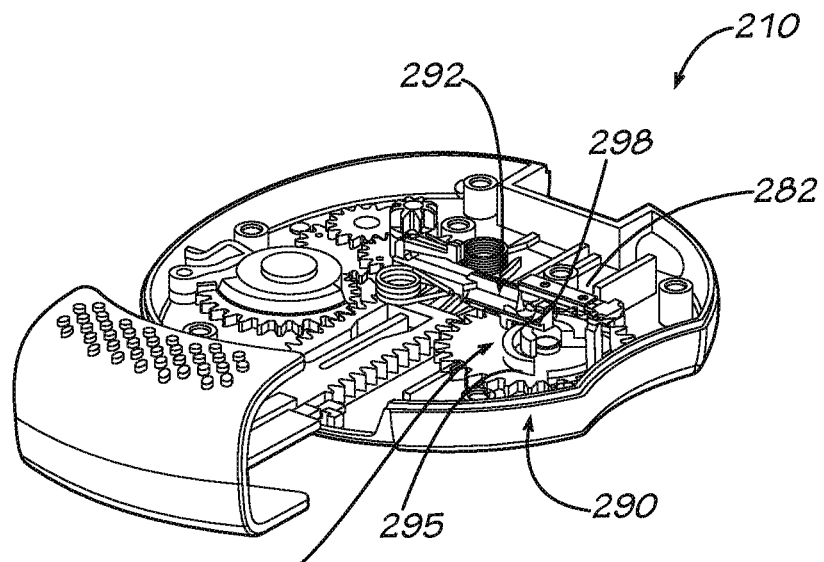
FIG. 48 is a perspective view of the lancing device of FIG. 47.

Referring now to FIGS. 47-48, a cartridge-based lancing device 210 according to a second example embodiment of the invention is depicted. The lancing device 210 is designed for use with a cartridge (not shown) holding a plurality of lancets 282 (one lancet is shown for illustration purposes). The lancets 282 and cartridge can be of the same or a different type as that described elsewhere herein. The lancing device 210 can include the same or different operational assemblies as described elsewhere herein.

The lancing device 210 includes a charging mechanism 290 that is similar to the charging mechanism 90 described above. In particular, the charging mechanism 290 includes a piston 292, a drive spring 293, a return spring 294, and an activation button (not shown) that are the same as or similar to those components in the embodiment of FIGS. 33-43. The lancing device 210 also includes a guide element 291, but instead of the guide being positioned on the operating handle 221 (e.g., on the elongate member that extends from the grip and into the housing), it is positioned on a rotary charging gear 201 such as the rotary gear of the cap-displacement mechanism.

The guide 291 includes a cam surface 295 that is engaged by a follower surface 298 of the piston 292 so that when the cam surface rides across the follower the piston is retracted against the biasing force of the drive spring 293 to a charged position. The cam surface 295 is ramped in a curved shape that is eccentric relative to the rotational axis of the rotary gear 201. When the operating handle 221 is pushed in from the depicted extended position to the retracted position (the "push" portion of the "push/pull" cycle, after the operating handle has been pulled out to the extended position to advance the lancets 282), the piston follower 298 is guided along the cam surface 295 further and further away from the rotational axis of the gear 201. As the piston follower 298 is thus driven away from the rotational axis of the gear 201, the piston 292 is retracted to its retracted/charged position ready for firing. When the piston 292 is in the retracted/charged position, the cam surface 295 has traveled completely past the end of the piston follower 298 so that the cam surface is not in the lancing stroke path.

In an alternative embodiment, a lancing device is provided with the charging mechanism but with a different or no cap-displacement mechanism (e.g., where lancets are provided without caps). In such embodiments, the charging mechanism includes a dedicated rotary gear that forms the guide element and its cam surface, instead of the shared rotary cap-displacement and charging gear 101/201. In another alternative embodiment, a lancing device is provided with the charging mechanism having a dedicated rotary charging gear 201 that is separate from the rotary cap-displacement gear 101, with these rotary gears 101 and 201 being driven by the same or separate rack gears of the operating handle.

While the invention has been described with reference to preferred and example embodiments, it will be understood by those skilled in the art that a variety of modifications, additions and deletions are within the scope of the invention, as defined by the following claims.

What is claimed is:

1. A medical device for using or dispensing medical items in a rotary cartridge, the rotary cartridge defining a cartridge gear, the medical device comprising:
a housing;
an operating handle movable between first and second positions and including a grip and a gear, wherein the operating handle is movable along a translational actuation motion between the first and second positions, the first handle position being a retracted position with the grip translated in and generally adjacent the housing, and the second handle position being an extended position with the grip translated away from the housing; and
an advancement mechanism operable to sequentially advance the medical items for use or dispensing, the advancement mechanism including a rotary drive gear assembly, an inter-gear unidirectional rotary drive assembly, and a pinion output gear, wherein the rotary drive gear assembly includes a first rotary gear and a second rotary gear that rotate about a common axis, the first gear is rotationally driven by the operating handle gear in a first angular direction and an opposite second angular direction when the operating handle is moved between the first and second positions, the second gear directly or indirectly rotationally drives the pinion output gear, and the pinion output gear rotationally drives the cartridge gear, wherein the inter-gear unidirectional rotary drive assembly operably interconnects the first and second drive gears so that the second gear is driven by and rotates with the first gear in the first direction but is not driven in co-rotation by the first gear in the opposite second direction, wherein the inter-gear unidirectional rotary drive assembly includes a first catch surface defined by a first catch element, a second catch surface defined by a second catch element, and a disengagement surface included on one of the first and second catch elements, wherein the catch surfaces are engaged to maintain the first and second gears in co-rotation in the first angular direction, at least one of the catch surfaces moves out of engagement when the first gear rotates in the opposite second direction, and the catch surface disengagement is caused by the disengagement surface moving a movable one of the catch elements.

2. The medical device of claim 1, wherein the operating handle includes an elongate member extending from the grip and into the housing, and the handle gear is a rack gear defined by the elongate member.

3. The medical device of claim 1, wherein the inter-gear unidirectional rotary drive assembly is provided by a ratcheting drive assembly with the first catch element provided by a pawl that extends from one of the first and second drive gears and that defines the first catch surface, the second catch element provided by a tooth that extends from the other one of the first and second drive gears and that defines the second catch surface, and the disengagement surface provided by a ramped surface defined by the pawl or the tooth and positioned adjacent the respective catch surface.

4. The medical device of claim 3, wherein the catch surfaces oppose each other so that, when the first drive gear is rotated in the first direction, the first catch surface contacts the second catch surface to rotationally drive the second drive gear along with the first drive gear; but when the first gear is rotated in the second opposite direction, the first catch surface is rotated away from the second catch surface, so the second gear is not rotationally driven by the first gear; and when the first gear is rotated further in the second angular direction, the ramped surface of the disengagement surface is engaged by the pawl or the tooth to temporarily displace, from an engaged to a disengaged position, at least one of the catch surfaces so that the first catch surface rotates past the second catch surface; and once the ramped surface has been cleared, the pawl or the tooth returns to the engaged position so that the catch surfaces are again in an opposing relationship with each other so that rotating the first gear again causes the second gear to rotate therewith.

5. The medical device of claim 3, wherein the pawl is provided by three cantilevered resilient pawl arms each extending from the second drive gear in a generally spiral arrangement, the tooth is provided by three ratchet drive teeth formed on an inner circular surface of the first drive gear, and the disengagement surface is provided by three ramped surfaces defined by the teeth and positioned adjacent the respective catch surfaces so that when the ratchet teeth rotate into contact with the resilient pawl arms then the ramped surfaces ride across and resiliently deflect the pawl arms to allow the ratchet teeth to bypass the pawl arms.

6. The medical device of claim 1, wherein the advancement mechanism further comprises a second-gear unidirectional rotary lock assembly that operably interconnects the first and second drive gears so that the second gear is free to be driven by and co-rotate with the first gear in the first direction but is locked from co-rotation in the opposite second direction, wherein the second-gear unidirectional rotary lock assembly includes a first lock surface defined by a first lock element, a second lock surface defined by a second retainer element, and a disengagement surface, wherein the lock surfaces are engaged to lock the second gear from rotation in the second direction, at least one of the lock surfaces moves out of engagement when the second gear rotates in the first direction, and the lock surface disengagement is caused by the disengagement surface moving a movable one of the catch elements.

7. The medical device of claim 6, wherein the second-gear unidirectional rotary lock assembly is provided by a ratcheting lock assembly with the first lock element provided by a tooth that extends from one of the second drive gear and the housing and that defines the first lock surface, the second retainer element is provided by a pawl that extends from the other one of the second drive gear and the housing and that defines the second lock surface, and the disengagement surface of the lock assembly is provided by a ramped surface defined by the pawl or the tooth and positioned adjacent the respective lock surface.

8. The medical device of claim 7, wherein the lock surfaces oppose each other so that, when the first drive gear is rotated in the second direction, with the second drive gear not driven in co-rotation with the first drive gear, the pawl lock surface contacts the tooth lock surface to secure the second gear in place; but when the first gear is rotated in the first direction, the tooth lock surface is rotated away from the pawl lock surface, so the second gear is not restrained from being rotationally driven by the first gear; and when the first gear is rotated further in the first direction, the ramped surface is engaged to temporarily displace, from an engaged to a disengaged position, the pawl and lock surface thereof, so that the tooth lock surface rotates past the pawl lock surface; and so once the ramped surface has been cleared, the pawl returns to the engaged position so that the lock surfaces are again in an opposing relationship with each other so that when the first gear is again rotated in the second direction the second gear is locked from co-rotating with the first gear.

9. The medical device of claim 7, wherein the pawl is provided by a single spring-biased pawl arm that is pivotally mounted to the housing, the tooth is provided by three ratchet drive teeth extending from the second drive gear, and the disengagement surface of the lock assembly is provided by a single ramped surface defined by the pawl and positioned adjacent the pawl lock surface so that when the ratchet teeth rotate into contact with the resilient pawl arm then the ramped surface rides across the teeth to resiliently deflect the pawl arm to allow the ratchet teeth to bypass the pawl arm.

10. The medical device of claim 1, further comprising an idler gear assembly including at least one idler gear, wherein the idler gear assembly is rotationally driven by the second gear of the drive gear assembly, and rotationally drives the pinion output gear.

11. The medical device of claim 1, further comprising a pinion gear assembly including the pinion output gear and a pinion input gear that co-rotate about a common axis.

12. A lancing device for using lancets in a rotary cartridge, the rotary cartridge defining a cartridge gear, the lancing device comprising:
a housing;
an operating handle that translates between retracted and extended positions and includes a grip, an elongate member extending from the grip and into the housing, and a rack gear defined by the elongate member, wherein the operating handle translates along a linear path between the first and second positions such that the first handle position is in a retracted position with the grip translated in and generally adjacent the housing, and wherein the second handle position is in an extended position with the grip translated away from the housing; and
an advancement mechanism operable to sequentially advance the lancets for use, the advancement mechanism including a rotary drive gear assembly, an inter-gear unidirectional rotary ratcheting drive assembly, a second-gear unidirectional rotary ratcheting lock assembly, and a pinion output gear, wherein the rotary drive gear assembly includes a first rotary gear and a second rotary gear that rotate about a common axis, the first gear is rotationally driven by the operating handle rack gear in a first angular direction and an opposite second angular direction when the operating handle is translated between the retracted and extended positions, the second gear directly or indirectly rotationally drives the pinion output gear, and the pinion output gear rotationally drives the cartridge gear,
wherein the inter-gear unidirectional rotary ratcheting drive assembly operably interconnects the first and second drive gears so that the second gear is driven by and rotates with the first gear in the first direction but is not driven in co-rotation by the first gear in the opposite second direction, wherein the inter-gear unidirectional rotary ratcheting drive assembly includes at least one inter-gear pawl that extends from the second drive gears and that defines a catch surface, and at least one inter-gear tooth that extends from the first drive gears and that defines a catch surface, and at least one inter-gear ramped surface defined by the inter-gear tooth and positioned adjacent the respective catch surface, wherein the catch surfaces engage each other to maintain the first and second drive gears in co-rotation in the first angular direction, the inter-gear pawl catch surface is moved out of engagement with the inter-gear tooth catch surface when the first gear rotates in the opposite second direction, and the catch surface disengagement is caused by the inter-gear ramped surface moving the inter-gear pawl, and
wherein the second-gear unidirectional rotary lock assembly operably interconnects the first and second drive gears so that the second gear is free to be driven by and co-rotate with the first gear in the first direction but is locked from co-rotation in the opposite second direction, wherein the second-gear unidirectional rotary ratcheting drive assembly includes at least one second-gear tooth that extends from the second drive gear and that defines a lock surface, at least one second-gear pawl that extends from the housing and that defines a lock surface, and at least one second-gear ramped surface defined by the second-gear pawl and positioned adjacent the respective lock surface, wherein the lock surfaces engage each other to lock the second gear from rotation in the second direction, the second-gear pawl lock surface moves out of engagement with the second-gear tooth lock surface when the second gear rotates in the first direction, and the lock surface disengagement is caused by the second-gear ramped surface moving the second-gear pawl.

13. The lancing device of claim 12, wherein the catch surfaces oppose each other so that, when the first drive gear is rotated in the first direction, the catch surface of the first gear contacts the catch surface of the second gear to rotationally drive the second drive gear along with the first drive gear; but when the first gear is rotated in the second opposite direction, the catch surface of the first gear is rotated away from the catch surface of the second gear, so the second gear is not rotationally driven by the first gear; and when the first gear is rotated further in the second angular direction, the inter-gear ramped surface is engaged by the inter-gear pawl to temporarily displace, from an engaged to a disengaged position, at least one of the catch surfaces so that the catch surface of the first gear rotates past the catch surface of the second gear; and once the inter-gear ramped surface has been cleared, the inter-gear pawl returns to the engaged position so that the catch surfaces are again in an opposing relationship with each other so that rotating the first gear again causes the second gear to rotate therewith.

14. The lancing device of claim 13, wherein the at least one inter-gear pawl is provided by three cantilevered resilient pawl arms each extending from the second drive gear in a generally spiral arrangement, the at least one inter-gear tooth is provided by three ratchet drive teeth formed on an inner circular surface of the first drive gear, and the at least one inter-gear ramped surface is provided by three ramped surfaces defined by the teeth and positioned adjacent the respective catch surfaces so that when the ratchet teeth rotate into contact with the resilient pawl arms then the ramped surfaces ride across and resiliently deflect the pawl arms to allow the ratchet teeth to bypass the pawl arms.

15. The lancing device of claim 12, wherein the lock surfaces oppose each other so that, when the first drive gear is rotated in the second direction, with the second drive gear not driven in co-rotation with the first drive gear, the inter-gear pawl lock surface contacts the inter-gear tooth lock surface to secure the second gear in place; but when the first gear is rotated in the first direction, the inter-gear tooth lock surface is rotated away from the inter-gear pawl lock surface, so the second gear is not restrained from being rotationally driven by the first gear; and when the first gear is rotated further in the first direction, the inter-gear ramped surface is engaged to temporarily displace, from an engaged to a disengaged position, the inter-gear pawl and lock surface thereof, so that the inter-gear tooth lock surface rotates past the inter-gear pawl lock surface; and so once the inter-gear ramped surface has been cleared, the inter-gear pawl returns to the engaged position so that the lock surfaces are again in an opposing relationship with each other so that when the first gear is again rotated in the second direction the second gear is locked from co-rotating with the first gear.

16. The lancing device of claim 12, wherein the at least one second-gear pawl is provided by a single spring-biased pawl arm that is pivotally mounted to the housing, the at least one second-gear tooth is provided by three ratchet drive teeth extending from the second drive gear, and the at least one second-gear ramped surface is provided by a single ramped surface defined by the pawl arm and positioned adjacent the pawl arm lock surface so that when the ratchet teeth rotate into contact with the resilient pawl arm then the ramped surface rides across the teeth to resiliently deflect the pawl arm to allow the ratchet teeth to bypass the pawl arm.

17. The lancing device of claim 12, further comprising an idler gear assembly including at least one idler gear, wherein the idler gear assembly is rotationally driven by the second gear of the drive gear assembly, and rotationally drives the pinion output gear.

18. The lancing device of claim 12, further comprising a pinion gear assembly including the pinion output gear and a pinion input gear that co-rotate about a common axis.

* * * * *